(12) United States Patent
Rouviere et al.

(10) Patent No.: US 6,461,856 B2
(45) Date of Patent: Oct. 8, 2002

(54) GENES ENCODING PICRIC ACID DEGRADATION

(75) Inventors: Pierre E. Rouviere; Dana M. Walters, both of Wilmington, DE (US); Rainer Russ, Kaiserslautern (DE)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/955,597

(22) Filed: Sep. 17, 2001

(65) Prior Publication Data

US 2002/0042117 A1 Apr. 11, 2002

Related U.S. Application Data

(62) Division of application No. 09/651,941, filed on Aug. 31, 2000, now Pat. No. 6,355,470.
(60) Provisional application No. 60/152,545, filed on Sep. 3, 1999.

(51) Int. Cl.[7] ............................. C12N 1/20; C12N 9/04; C12N 1/14; C12N 1/68; C12N 21/04
(52) U.S. Cl. ............... 435/252.3; 435/190; 435/252.33; 435/252.35; 435/254.11; 435/320.1; 536/23.2
(58) Field of Search ..................... 435/190, 252.3, 435/252.33, 252.35, 254.11, 320.1; 536/23.2

(56) References Cited

U.S. PATENT DOCUMENTS 5,478,743 A 12/1995 Perkins et al. ............ 435/262.5
5,543,324 A 8/1996 Rajan et al. ............. 435/252.4

OTHER PUBLICATIONS

Erickson, J. Bacteriol. 41:277 (1941).
Moore, J. Gen. Microbiol., 3:143 (1949).
Gundersden et al., Acta. Agric. Scand. 6:100 (1956).
Wyman et al., Appl. Environ. Microbiol. 37(2):222 (1979).
Kearney et al., Chemosphere, 12 (11–12): 1583 (1983).
Lenke et al., Appl. Environ. Microbiol. 58(9): 2933 (1992).
Ebert et al., Bacateriol. 181(9): 2669–2674 (1999).
Murphy, et al., direct submission, Oct. 1, 1996 GENBANK.
Johansen, et al., GENBANK, Acc No. AJ243528.
Klenk, H. P. et al., Nature 390 (6658), 364–370 (1997).
Bult, C. J. et al., Science 273 (5278), 1058–1073 (1996).
Eaton, R. W. J. Bacteriol. 178 (5), 1351–1362 (1996).
Grundy, F. J. et al., Mol. Microbiol. 10:259–271 (1993).
Blattner, F. R. et al., RL Science 277: 1453–1474 (1997).
Smith, D. R. et al., J. Bacteriol. 179:7135–7155 (1977).
Redenbach, M., et al., Mol. Microbiol. 21(1), 77–96 (1996).
Bechman, D. L. et al., Gene 107: 171–172 (1992).

*Primary Examiner*—Ponnathapu Achutamurthy
*Assistant Examiner*—Y. Pak

(57) ABSTRACT

A 12 kb gene cluster has been isolated from *Rhodococcus erythropolis* containing several open reading frames implicated in the degradation of picric acid. The gene cluster contains 12 ORF's, all of which were isolated by a method employing differential gene display.

7 Claims, 9 Drawing Sheets

ORF 1   Transcription Factor

ORF 2   Dehydratase

ORF 3   F420-dpdt Dehydrogenase #1

ORF 4   Aldehyde Dehydrogenase

ORF 5   Acetyl CoA Synthetase

ORF 6   Glyoxalase

ORF 7   Transcription Regulator

ORF 8   F420/NADPH oxidoreductase

ORF 8.1 Conserved Hypothetical

ORF 9   F420-dpdt Dehydrogenase #2

ORF 10  Enoyl-CoA Hydratase

ORF 11  Acyl-CoA Dehydrogenase

SEQUENCE LISTING

<160> NUMBER OF SEQ ID NOS: 28

<210> SEQ ID NO 1
<211> LENGTH: 12523
<212> TYPE: DNA
<213> ORGANISM: Rhodococcus erythropolis HL PM-1

<400> SEQUENCE: 1
cgcctgaccg accgcttcac cctgctgacc cgcggcaacc ggggtgcgcc gacgcggcag      60
cagaccctgc ggttgtgtat cgactggagc ttcgagttgt gcaccgccgg tgagcaactg     120

-continued

| | |
|---|---|
| gtgtggggc gggtggcggt cttcgcgggg tgcttcgaac tcgatgccgc ggagcaggtg | 180 |
| tgtggcgagg gcctggcctc gggcgagtta ttggacacgc tgacctccct ggtggagaag | 240 |
| tcgatcctga tccgggagga atccgggtcg gtggtgcttt tccggatgct cgagactctc | 300 |
| cgtgagtacg gctacgagaa gctcgagcag tccggcgagg cattggatct gcgtcgccgg | 360 |
| caccggaatt ggtacgaggc gttggcgctg gatgcgaag ccgagtggat cagcgcgcgc | 420 |
| caactcgact ggatcacccg gctgaagcgg gaacaaccga atctgcggga ggccctcgaa | 480 |
| ttcggcgtcg acgacgatcc cgtcgccggt ctgcgcaccg ccgccgcact gttcctgttc | 540 |
| tggggctctc agggcctcta caacgagggg cggcgctggc tcggccagct gctcgcccgc | 600 |
| cagagcggcc caccgacggt cgagtgggtc aaggccctcg aacgcgccgg catgatggcc | 660 |
| aatgtgcagg gtgatctgac tgccggagcc gcactcgtgg cggaggggcg agcgctcact | 720 |
| gcccacacga gtgaccccat gatgcgggct ctcgttgcat acggcgatgg catgcttgcc | 780 |
| ctctacagcg gtgatctggc gcgtgcgtct tcggacctcg aaaccgctct gacggagttc | 840 |
| accgcgcgcg gtgaccgaac gctcgaagta gccgcactgt acccgttggg gttggcgtac | 900 |
| ggactgcgcg gctcgacgga ccggtcgatc gaacgtctcg agcgcgttct cgcgatcacg | 960 |
| gagcagcacg gcgagaaaat gtatcggtcg cactcgttgt gggctctggg tatcgccctg | 1020 |
| tggcggcacg gggacggcga tcgcgcggtc cgcgtgctca gcagtcgct ggaggtgacc | 1080 |
| cggcaagtgc acggcccacg tgtcgccgcg tcctgtctcg aggcactggc ctggatagcc | 1140 |
| tgcggaatgc gtgacgaacc gagggctgcg gttctgttgg gagccgcaga agagttggcg | 1200 |
| cgatcagtgg gcagtgccgt ggtgatctac tccgatcttc ttgtctacca tcaggaatgc | 1260 |
| gaacagaagt ctcgacggga actcggggac aaaggattcg cggcggccta ccgcaagggt | 1320 |
| cagggactcg gtttcgacgc ggccatcgcc tatgccctcc gcgagcaacc gccgagcacc | 1380 |
| tccggaccca ccgccggtgg gtcgacgcga ctgaccaagc gggaacgcca agtcgccggc | 1440 |
| ctcatcgccg aaggtctcac caaccaggcc atcgccgacc gcctggtgat ctctccacgg | 1500 |
| accgcgcaag gcacgtggga gcacatcctg gccaagctgg gttttcacgtc ccgggcgcag | 1560 |
| gtcgcggcct gggtcgtcga gcggaccgac gactgaatgg aacacctccg ctcgcgttga | 1620 |
| acgcggcagt cggtgacgac cgcgaccgcg ggtcggtccc tggaatcgcg acgtaaacgg | 1680 |
| ttctccccga acatatgtgg cctttcgttt cgcgttgctg cgcgcccgcc atttcccgtc | 1740 |
| gtgggaccga atcgcccgcc acgcaccggc cgccggaaat ctgctccctc ttgacagcgg | 1800 |
| gcggtggtgc tcgtaacgtc cgtggagttc caaataatga tgtcagttca gcatagtgaa | 1860 |
| cggagcttgt gatggggttc accggaaatg tcgaggcgct gtcgggaatc cgagtggtcg | 1920 |
| acgccgcgac gatggtcgcc ggccccttgg gtgcgtcgct gctcgccgat tcggtgccg | 1980 |
| acgtcatcaa ggtcgagccg atcggcggcg acgagtcgcg gacgttcggg ccgggacgag | 2040 |
| acggcatgag tggtgtctat tccggcgtga accgaaacaa gcgcgccctc gcgctcgacc | 2100 |
| ttcgacgga ggcgggccgt gacctgttcc acgagctgtg ctcgacagcg gacgtgctca | 2160 |
| tcgagaacat gctgccggcg gtacgggaac gattcgggct gactgccgcc gagcttcgcg | 2220 |
| aacggcaccc tcacctgatc tgcctcaatg tcagcgggta cggcgagacc ggccccctcg | 2280 |
| cgggtcgccc cgcaatggac ccggtggctc aggcgctcac cggactcatg caggcgaccg | 2340 |
| gtgagcgctc ggggaggtcg ctcaaggccg gtccgcccgt cgccgacagt gcggcgggct | 2400 |
| acctggtcgc gatcgccgcc ctcgtcgcgc tcttcgcgaa acagcgcacg ggggaggggc | 2460 |
| aaagtggctc ggtgtccctg gtgggggcgc tgttccattt gcagacgccg tggctggggc | 2520 |

-continued

```
agtacctcct ggccgactac atccagggca aggtgggcaa cggcagcaat ttctacgcgc   2580
cgtacaacgc ctatacgacc cgtgacggcg gcgcggtgca tgtcgttgcc ttcaacgacc   2640
gccacttcgt caagctcgcc cgggcgatgg gtgccgaggc tctgatcgac gatccgcgct   2700
tcgcgcaggc cgcatcccga ctggagaacc gtgaggccct cgacgacgcc gtcgcaccct   2760
ggttcgccga ccgcgaccgg gacgacgtgg ttgcactgct ctcggcccac gacatcatct   2820
gtgccccgat tctcgcgtac gacgaggccg tcaggcatcc ccagatccag gcactggacc   2880
tcgtcgtcga catcacccac gacgaactcg gaccgctgca ggttccgggt ctcccggtca   2940
agctctcggg cacccgggga cacgtacacc gcccaccgac gtcgttgggc gagcacacca   3000
ccgagattct cagcgatctc ggctacaagg acgaccggat tgcggccctc cgggccgaac   3060
gggtcgtccg atgaccacag aacatggcga aggaaccac caatgaaggt cggaatcagg   3120
atcccgggag caggaccgtg ggcagggccc gaggcgatca cggaggtgtc gcggttcgct   3180
gagaagatcg gcttcgactc gctctggatg actgatcatg tggccttgcc gacccgagtc   3240
gagacggcgt acccgtacac cgacgacggc aagttcctgt gggatccggc cacgccgtac   3300
ctcgactgcc tcacgtcgtt gacgtgggcg gcggccgcga ccgagcggat ggagctcggc   3360
acgtcgtgcc tcatcctgcc gtggcgtccg ctcgtccaga ccgccaagac actggtgagc   3420
atcgacgtga tgtcgcgcgg ccggctgtcg gtcgccatcg gcgtgggctg gatgaaggag   3480
cagttcgagc tgctgggagc gcctttcaag gaccggggga gcggaccac ggagatggtc   3540
aacgcgatgc ggcacatgtg gaaggaagac gaggtcgcct tcgacggtga gttctaccaa   3600
ctccacgact tcaagatgta tccgaagccg gtgcggggca cgatccccgt ctggttcgcg   3660
ggatacagca ccgcctccct cgccgtatcc gccgccatcg gcgacgggtg gcacccattg   3720
gcgatcgggc cggaggagta cgccggctac ctggccaccc tgaagcaata cgccgaggaa   3780
gccggccgcg acatgaacga aatcaccctc accgcgcggc ctctgcggaa ggcgccgtac   3840
aacgccgaga cgatcgaagc gtacggcgaa ctcggtgtca cccacttcat ctgcgacacg   3900
tcgttcgagc acgacacccct cgaagcaacc atggacgagc tcgccgagct tgccgacgcc   3960
gtcctcccca ccgcacacaa cctgcccttga cggcccggcg gaagaaagga cgagaattgt   4020
gcaggcactc acctcatcgg ttcccctcgt catcggcgac caactgaccc catcgtcgac   4080
gggggcgacc ttcgactcga tcaacccggc cgacgggtcg cacctggcca gcgtcgccga   4140
ggccacggcc gcggacgtcg cgcgtgcggt cgaagccgcg aaggcggcgg ccaggacgtg   4200
gcagcgcatg cgcccggccc agcgaacccg cctgatgttc cgctacgccg cgctgatcga   4260
ggaacacaag accgagctcg cccagctgca gagtcgggac atgggcaagc ccatccgcga   4320
gtcgctcggg atcgacctgc cgatcatgat cgagacgctc gagtacttcg cgggcctcgt   4380
gaccaagatc gagggccgaa cgacgccggc gcccggccgt ttcctcaact acaccctgcg   4440
tgagccgatc ggtgtggtgg gcgccatcac tccctggaat tttcctgcag tgcaggcggt   4500
ctggaagatc gccccggctc ttgcgatggg caacgccatc gtgctgaagc ctgcgcagct   4560
cgcaccactc gtgcccgtgg cactcggcga gctcgccctc gaggcgggtc tgccgcccgg   4620
gctggtcaac gtcctgcccg gccgcgggtc ggtagcgggt aacgccttgg tgcagcaccc   4680
atcggtcggc aaggtgacgt tcaccggctc gaccgaggtc ggccagcaga tcggccggat   4740
ggcggccgac cgcctcatca cggcttcgct ggagctgggc ggaaagtctg cgctcgtggc   4800
gttcggcgac tcgtccccga aggcggtcgc agccgtggtc ttccaggcga tgtacagcaa   4860
```

```
ccagggtgag acctgcacgg cgccgagcag gttgctcgtc gagcggccga tctacgacga    4920
ggtggtcgag ctcgtccagg cacgtgtcga ggccgcccgg gtgggcgacc cgctcgaccc    4980
cgacacggaa atcggcccgt tgatcagtgc cgagcagcgg gagtcggtcc actcgtacgt    5040
cgtctccggg accgaggaag gcgccacgct gatcagcggt ggcgaccagt cgccgaccgg    5100
agcgccggag cagggattct actaccgtcc gacgctcttc tccggagtca ccgcggacat    5160
gcgcatcgct cgggaggaga tcttcggacc cgtgctgtcg gtgctgccgt tcgagggaga    5220
agaggaggcg atcaccctgg ccaacgacac cgtcttcggg ctggccgcgg gcgtcttcac    5280
ccgcgatgtg ggccgcgcac tgcggttcgc gcagacgctc gacgccggca acgtgtggat    5340
caacagctgg ggagtgctca acccggcgtc gccgtatcga ggcttcgggc agagcggcta    5400
cggcagcgac ctcggccagg cggccatcga aagcttcacc aaggagaaga gcatatgggc    5460
acgcctggac tgacctccgg gacatcgagg tcacggacca tcaggcggtt gatcgacgcc    5520
cgccacaccc aggattggaa gccagcggcg gactacacga tcaccgagga cgccctcttc    5580
tcacgcgacc ccgacgccgt ggccgtgctg cgcggggggc tccacacgcc cgagaaggtg    5640
acgttcggtc aggtacagca cgccgctgtg cgcgtcgccg gtgtcctccg gtcccgcggg    5700
gtcgagcccg gtgaccgcgt ggtcctgtac ctcgacccct cggtggaggc cgccgaggtc    5760
gtcttcgggg tgctcgtcgc cggcgccgtg ctcgtgcccg tcccgcgact gctcaccggt    5820
acctcggtgg cgcaccggct cgccgactcg ggcgcgactg tgctggtcac ggacggtccg    5880
ggcgtcgacc ggctggagtc gacaggatgt tccctgcacg acgtcgacgt gctcacggtg    5940
gacggcgccc acggcgcgcc gctcggggac ctgacccgcc gggtcgaccc gctcgccccg    6000
gtgccgcggc ggtcctcgga tcttgctctg ctgatgtaca cgtcgggcac cagcggcccg    6060
cccaagggca tcgttcacgg ccatcgggtc ctgctcggac atgcgggggt cgactacgcc    6120
ttcgaactgt tcaggccggg tgacgtctat ttcggcactg cggactgggg gtggatcggc    6180
ggcctgatgc tcgggttgct ggttccgtgg tctctcggcg ttcctgtcgt ggctcaccgg    6240
ccgcagcgtt tcgatcccgg cgccaccctg gacatgctga ccggtacag cgtgacgacc    6300
gccttcctgc cggcgtcggt tcttcggatg tttgccgaac acggggaacc ggcccagcgg    6360
cgtctgcggg cggtggtgac cggaggcgag cccgccggcg cggtggaact cggctgggcc    6420
cggcggcatc tcagcgacgc cgtcaacaag gcctacggtc agaccgaggc caacgcgctc    6480
atcggcgact ccgctgttct cggatccgtc gacgacgcga ccatgggcgc tccgtatccc    6540
gggcaccgca tcgcgctcct ggacgacgcg ggcactcacg tcgcgcccgg tgaggtcggt    6600
gagattgcgc tggaacttcc ggattcggtt gcgctgctcg gctattggga tgcgtcgtcg    6660
gctagtgtgg tacctcccgc cgggagttgg caccggacag gcgacctggc acggctcgca    6720
catggacgcc ggctggagta cctcggccgc gccgacgacg tgatcaagag ccgcggctac    6780
cgcatcggtc cggcggagat cgaagaggca ctgaagcgtc accccaggt cctggacgcg    6840
gcggcggtag ggctgcccga cccggagtcg gggcagcagg tcaaggcatt cgtccacctc    6900
gctgccggcg aactcaccga ggagatttcg gcggaactcc gtgaactcgt cgccgccgcg    6960
gtcggcccac acgcacgccc ccgcgagata gaggcagtcg cagcgttgcc gcgcacggag    7020
accggaaagg tccggcggcg ggaactggtg ccgccctcgg cttagcattc ggcgactgcc    7080
gcggcctcgt ggagcgccat ccacccaccc gaacacagaa gtgcaagaag aaggacgaag    7140
caatgcgaaa gttctggcac gtcggcatca atgtgaccga catggacaaa tcgatcgact    7200
tctatcggcg aatcggtttc gaggtagtgc aggatcggga ggtggaggac agcaaccttg    7260
```

```
cgcgggcatt catggtcgag ggtgccagca agctccgctt cgcacacttg cgcctgaacg    7320
actccccgga cgaggcgatg ctggacctca tcgagtggag ggacgcacgt tccgaggggc    7380
gagcgcagag cgacctcgtg cacccgggac tctgccgatt ctcgatcctc accgacgaca    7440
tcgacgccga gtatgcacgg ctggcggacg acggcgtcca gttcctgcac gcgccgcaga    7500
cgatcatggg tccggacggc gtcaagggct ggcggctgct cttcgcgcgc gatcccgacg    7560
gcacgctgtt ccatttcgcc gaacttgtgg ggcaggccgc tacggtcagc tgacagcatt    7620
cgcacgacga aggtaggaac ccttgaccaa ggcagaagtc ccgggaagca gcgcgactga    7680
cgagcggggc gagcaatcca gcgagcagct ggtgcccgcc atctcgcgcg caacccgcgt    7740
actcgagaca ctggtccagc agtccaccgg agccacactc accgagttgg ccaagcggtg    7800
cgctctggcg aagagcacgg catcggtcct gctccggacc atggtggtcg agggcctcgt    7860
cgtgtacgac caggagacgc gccggtacaa cctcggcccg ctgctcgtgg agttcggcgt    7920
ggctgcgatc gcgcgaacat cggcggtcgc cgcgtcgcgg acgtacatgg agtggttggc    7980
cgagcggacc gagctggcat gtctcgccat ccagccgatg ccggacggtc acttcacggc    8040
gatcgcgaag atcgagagcc gcaaggccgt caaggtcacc atcgaggtcg gctctcgctt    8100
cggtcgagac actccgttga tcagccgact cgcggcggca tggccgagca ggggtcgccc    8160
ggagcttgtc gagtaccccg ccgatgagct cgacgagctc cgggcgcagg gctacggcgc    8220
tgtctatggc gaatatcgac cggaactcaa cgtcgtgggg gtcccggtgt cgaccgaga    8280 cggcgagccg tgtctgttca tcgccctgct cggtatcggc gacgatctca cagccgacgg    8340
tgtggccggg atcgccgact acctcgtcac ggtttcgcgg gagatcagct cgcatatcgg    8400
cggccgcatt ccggcggact acccgactcc tgtcggggcc cccgacctcg cgccgggcg    8460 cggctgaccg agccccccgat ttcaatcaag cggcggcccc accggggcct gccgctccga    8520
gtcgaccccc aacggtcggc tgaccacctc cggtgcaacg cgtcggaggt gtcccgtccc    8580
aatgtgtagg agacagacat gaagagcagc aagatcgccg tcgtcggcgg caccggaccc    8640
cagggaaagg ggctggccta ccggttcgcg gcggccggct ggcctgtcgt catcggatcg    8700
cgttctgccg aacgcgcgga ggaggcggcc ctcgaggtgc gcagacgcgc cggtgacggc    8760
gccgtggtca gcgccgccga caatgcgtcg gcagctgccg actgtcccat catcctgctg    8820
gtcgtcccat acgacggcca tcgtgagctg gtttcggaac tggcacccat cttcgcgggc    8880
aagctcgtcg tcagctgcgt gaatccgctc ggcttcgaca agtccggggc ctacggtttg    8940
gacgtcgagg aagggagcgc cgccgagcaa ctgcgcgacc tcgtgcccgg tgccacggtg    9000
gtcgctgcct ttcaccatct gtcggcggtc aacctctggg aacatgaggg ccccccttccc    9060 gaggatgtgc tcgtgtgcgg cgacgatcgg tccgcgaagg acgaggtggc tcggctcgca    9120
gtcgcgatca ccgccggcc gggcatcgac ggaggggcgc tgcgggtggc gcggcagctc    9180
gaaccgttga ccgccgttct catcaatgtc aaccggcgct acaagacgct ctccggtctc    9240
gccgtgaacg gggttgttca tgatccacga gctgcgtgag taccttgcgc tgccgggccg    9300
tgccgaggac ctgcaccgca ggttcgccga cgacacgctg gccctgttcg cggaattcgg    9360
gctgcaggtc gagggcttct ggcacgaggc aggcaaccgt gccccggatcg tgtacctgtt    9420 ggcgttcccc gacttcgagg ccgcggacgc gcattgggcc cggttccagg ccgaccccg    9480 gtggtgtgcg ttgaaggcac gcaccgagag cgacgggccg ctcatctcgg agatccggag    9540
cacgttcctg atcaccccgt catacgcccg ctcctgagcg gcaccgaacg aggctggact    9600
```

| | |
|---|---|
| gactcttgac cgtcgccgtg ttctgcccct aacctgttcc atatagtgat tcgagttcaa | 9660 |
| catcatgaag agaagttcga tgatcaaagg catccagctc catggttggg ctgacgggcc | 9720 |
| gcagatggtc gaagtggccg agatcgccgc tgggagtttc gaaaccgtct ggctcagtga | 9780 |
| ccaactccag tcccgaggcg tcgccgttct cctcggcgca atcgctgcgc gcaccggtgt | 9840 |
| cggagtcggc actgcagtga cctttcccct cgggcggaac cccctcgaga tggcatccag | 9900 |
| catggccacc ctggcggagt tcatgcccga aggacgtcgg gtcaccatgg aatcggcac | 9960 |
| cggaggtggg ctggtgagtg cgctcatgcc gctgcagaac ccgatcgacc gcgtggccga | 10020 |
| gttcatcgcg atgtgccggc ttctctggca gggcgaagcg atccgaatgg gtgactaccc | 10080 |
| acagatctgt accgccctcg gcttgcgtga ggatgctcgg gcgtcgttct cctggacgag | 10140 |
| caagcccgac gtgcgcgtcg tcgtcgccgg cgccggaccg aaagtgctgg agatggccgg | 10200 |
| cgaactcgca gacggcgtca tctgcgccag caatttcccg gcccacagcc tcgcggcctt | 10260 |
| ccgtagcggc cagttcgacg cggtgagcaa cctcgatgcg ctcgaccggg gccgaaagcg | 10320 |
| cagtcggcgg ggggagttca cccggatcta cggcgtgaac ctgtccgtgt ctgccgaccg | 10380 |
| ggagagtgcc tgcgcggccg cgcggcgaca ggcgacactc attgtgagcc aacagcctcc | 10440 |
| agagaatctg caccgggtcg gctttgagcc ctccgactac gccgccaccc gagcggcgct | 10500 |
| caaagccgga gacggcgtag acgcagccgc cgacctcctc ccacaggaag tcgcggacca | 10560 |
| actcgtggtc tcgggcacgc ccggcgactg catcgaggcg ctggccgagc tgctcgggta | 10620 |
| cgcggaggat gccggattca ccgaggccta catcggtgcc ccggtcggcc cggacccacg | 10680 |
| cgaggcggtc gagctcctca cgtcccaggt cctgccggag ctcgcatgag cgccggcacg | 10740 |
| caggcaaccc gggacctgtg cccggccgaa caccacgacg gtctggtcgt cctgacgctc | 10800 |
| aatcgtcccg aggcgcgcaa cgccctcgac gtaccctgc tcgaggcgtt cgccgctcgg | 10860 |
| cttgccgagg aaaacgcgc gggcgccggc gtcgtcctcg tgcgcgcgga agggccggcg | 10920 |
| ttctgcgcag gagccgatgt gcgttccgac gacggcacgg cgaccggccg accgggcctc | 10980 |
| cggcgccgtc tcatcgagga gagcctcgac ctgctgggcg actacccggc ggcggtggtc | 11040 |
| gcggtgcagg gcgccgcgat cggcgccggg tgggcaatag ccgcggcagc ggacatcacg | 11100 |
| ctggcctcgc ctaccgcttc gttccgattt cccgagctcc cactcggatt cccgcccct | 11160 |
| gacagcacgg tgcgcatact cgaagccgcc gtcggcccgg cgcgggcgct gcggctcctg | 11220 |
| gccctgaacg agcgcttcgt cgccgacgac ctggccaggc tcggtctggt ggacgtcgtt | 11280 |
| cccgaggatt cgctcgacgt gacggcgcgc gagacggccg cccgactcgc ggttcttccc | 11340 |
| ctcgagttgc tgcgcgatct caaaacaggc ctctccgccg ggaagcggcc ccctccatc | 11400 |
| gaccgaccag cctcgaaagg cagtcatgag cactagcatt cacattcaga ccgacgagca | 11460 |
| ggcgcacctc cgcaccactg cccgggcatt cctggccaga cacgctcccg cgctcgacgt | 11520 |
| gcgcatctgg gacgaggcgg ggaaataccc cgagcacctg ttccgcgaga tcgcccgcct | 11580 |
| cgggtggtac gacgtggtgg ccggagacga ggtcgtcgac ggtacggccg gcctgctgat | 11640 |
| cacgctctgc gaagagatcg gccgggcgag ttcggacctc gtggccttgt tcaacctgaa | 11700 |
| cctcagtggg ctgcgcgaca tccaccgctg gggcacgccc gaacagcagg agacgtacgg | 11760 |
| tgcaccggtg ctggccggcg aggcgcgcct gtcgatcgcg gtgagcgaac ccgacgtggg | 11820 |
| ctcggacgcc gcgagcgtgg ccacgcgcgc cgagaaggtc ggggactcgt ggatcctcaa | 11880 |
| cggccagaag acctactgcg agggcgcggg actaaccggc gcagtaatgg aactcgtcgc | 11940 |
| ccgagtggga gggggtggtc gcaagcgcga ccaactcgcc atatttctgg tgccggtcga | 12000 |

```
tcatccgggg gtcgaggtcc gccgcatgcc cgcgctcggc cggaacatca gcggcatcta    12060
cgaggtcttc ctgcgggacg ttgcgcttcc ggcgacggcg tgctgggtg agcccggtga     12120 aggatggcag atcctcaagg aacgtctggt gctcgagcgg atcatgatca gttccggctt    12180
cctcggcagc gtcgccgcgg tactcgacct gacggtccac tacgccaacg agcgcgagca    12240
gttcggcaag gcactctcga gctatcaggg cgtgaccttg cccctcgccg agatgttcgt    12300
caggctcgac gcggcccagt gcgcggtacg ccgttcggcc gacctcttcg acgcgggtct    12360
gccgtgcgag gtggagagca cgatggcgaa gttcctctcc ggccagctct acgcggaggc    12420
ctctgctctg gcgatgcaga ttcagggcgc ctacggctat gtgcgcgacc atgccttgcc    12480
gatgcaccac tccgacggga tccccgggta ccgagctcga att                     12523

<210> SEQ ID NO 2
<211> LENGTH: 1596
<212> TYPE: DNA
<213> ORGANISM: Rhodococcus erythropolis HL PM-1

<400> SEQUENCE: 2
cgcctgaccg accgcttcac cctgctgacc cgcggcaacc ggggtgcgcc gacgcggcag      60
cagaccctgc ggttgtgtat cgactggagc ttcgagttgt gcaccgccgg tgagcaactg     120 gtgtggggc gggtggcggt cttcgcgggg tgcttcgaac tcgatgccgc ggagcaggtg      180
tgtggcgagg gcctggcctc gggcgagtta ttggacacgc tgacctccct ggtgagaag      240 tcgatcctga tccgggagga atccggtcg gtggtgcttt tccggatgct cgagactctc      300
cgtgagtacg gctacgagaa gctcgagcag tccggcgagg cattggatct gcgtcgccgg     360
caccggaatt ggtacgaggc gttggcgctg gatgcggaag ccgagtggat cagcgcgcgc     420
caactcgact ggatcacccg gctgaagcgg gaacaaccga atctgcggga ggccctcgaa     480
ttcggcgtcg acgacgatcc cgtcgccggt ctgcgcaccg ccgccgcact gttcctgttc     540 tgggctctc agggcctcta caacgagggg cggcgctggc tcggccagct gctcgcccgc     600
cagagcggcc caccgacggt cgagtgggtc aaggccctcg aacgcgccgg catgatggcc     660
aatgtgcagg gtgatctgac tgccggagcc gcactcgtgg cggaggggcg agcgctcact     720
gcccacacga gtgaccccat gatgcgggct ctcgttgcat acggcgatgg catgcttgcc     780
ctctacagcg gtgatctggc gcgtgcgtct tcggacctcg aaaccgctct gacggagttc     840
accgcgcgcg gtgaccgaac gctcgaagta gccgcactgt acccgttggg gttggcgtac     900
ggactgcgcg gctcgacgga ccggtcgatc gaacgtctcg agcgcgttct cgcgatcacg     960
gagcagcacg gcgagaaaat gtatcggtcg cactcgttgt gggctctggg tatcgccctg    1020
tggcggcacg gggacggcga tcgcgcggtc gcgtgctcg agcagtcgct ggaggtgacc     1080
cggcaagtgc acgcccacg tgtcgccgcg tcctgtctcg aggcactggc ctggatagcc     1140
tgcggaatgc gtgacgaacc gagggctgcg gttctgttgg agccgcaga agagttggcg     1200 cgatcagtgg gcagtgccgt ggtgatctac tccgatcttc ttgtctacca tcaggaatgc    1260
gaacagaagt ctcgacggga actcgggac aaaggattcg cggcggccta ccgcaagggt     1320
cagggactcg gtttcgacgc ggccatcgcc tatgccctcc gcgagcaacc gccgagcacc    1380
tccggaccca cgccggtgg gtcgacgcga ctgaccaagc gggaacgcca agtcgccggc     1440
ctcatcgccg aaggtctcac caaccaggcc atcgccgacc gctggtgat ctctccacgg     1500 accgcgcaag ggcacgtgga gcacatcctg gccaagctgg gtttcacgtc ccgggcgcag    1560
```

-continued

```
gtcgcggcct gggtcgtcga gcggaccgac gactga                    1596
```

<210> SEQ ID NO 3
<211> LENGTH: 532
<212> TYPE: PRT
<213> ORGANISM: Rhodococcus erythropolis HL PM-1

<400> SEQUENCE: 3

```
Arg Leu Thr Asp Arg Phe Thr Leu Leu Thr Arg Gly Asn Arg Gly Ala
 1               5                  10                  15

Pro Thr Arg Gln Gln Thr Leu Arg Leu Cys Ile Asp Trp Ser Phe Glu
            20                  25                  30

Leu Cys Thr Ala Gly Glu Gln Leu Val Trp Gly Arg Val Ala Val Phe
        35                  40                  45

Ala Gly Cys Phe Glu Leu Asp Ala Ala Glu Gln Val Cys Gly Glu Gly
    50                  55                  60

Leu Ala Ser Gly Glu Leu Leu Asp Thr Leu Thr Ser Leu Val Glu Lys
65                  70                  75                  80

Ser Ile Leu Ile Arg Glu Glu Ser Gly Ser Val Val Leu Phe Arg Met
                85                  90                  95

Leu Glu Thr Leu Arg Glu Tyr Gly Tyr Glu Lys Leu Glu Gln Ser Gly
            100                 105                 110

Glu Ala Leu Asp Leu Arg Arg His Arg Asn Trp Tyr Glu Ala Leu
        115                 120                 125

Ala Leu Asp Ala Glu Ala Glu Trp Ile Ser Ala Arg Gln Leu Asp Trp
    130                 135                 140

Ile Thr Arg Leu Lys Arg Glu Gln Pro Asn Leu Arg Glu Ala Leu Glu
145                 150                 155                 160

Phe Gly Val Asp Asp Pro Val Ala Gly Leu Arg Thr Ala Ala Ala
                165                 170                 175

Leu Phe Leu Phe Trp Gly Ser Gln Gly Leu Tyr Asn Glu Gly Arg Arg
            180                 185                 190

Trp Leu Gly Gln Leu Leu Ala Arg Gln Ser Gly Pro Pro Thr Val Glu
        195                 200                 205

Trp Val Lys Ala Leu Glu Arg Ala Gly Met Met ala Asn Val Gln Gly
    210                 215                 220

Asp Leu Thr Ala Gly Ala Ala Leu Val Ala Glu Gly Arg Ala Leu Thr
225                 230                 235                 240

Ala His Thr Ser Asp Pro Met Met Arg Ala Leu Val Ala Tyr Gly Asp
                245                 250                 255

Gly Met Leu Ala Leu Tyr Ser Gly Asp Leu Ala Arg Ala Ser Ser Asp
            260                 265                 270

Leu Glu Thr Ala Leu Thr Glu Phe Thr Ala Arg Gly Asp Arg Thr Leu
        275                 280                 285

Glu Val Ala Ala Leu Tyr Pro Leu Gly Leu Ala Tyr Gly Leu Arg Gly
    290                 295                 300

Ser Thr Asp Arg Ser Ile Glu Arg Leu Glu Arg Val Leu Ala Ile Thr
305                 310                 315                 320

Glu Gln His Gly Glu Lys Met Tyr Arg Ser His Ser Leu Trp Ala Leu
                325                 330                 335

Gly Ile Ala Leu Trp Arg His Gly Asp Gly Asp Arg Ala Val Arg Val
            340                 345                 350

Leu Glu Gln Ser Leu Glu Val Thr Arg Gln Val His Gly Pro Arg Val
        355                 360                 365
```

-continued

```
Ala Ala Ser Cys Leu Glu Ala Leu Ala Trp Ile Ala Cys Gly Met Arg
    370                 375                 380

Asp Glu Pro Arg Ala Ala Val Leu Leu Gly Ala Ala Glu Glu Leu Ala
385                 390                 395                 400

Arg Ser Val Gly Ser Ala Val Val Ile Tyr Ser Asp Leu Leu Val Tyr
                405                 410                 415

His Gln Glu Cys Glu Gln Lys Ser Arg Arg Glu Leu Gly Asp Lys Gly
            420                 425                 430

Phe Ala Ala Tyr Arg Lys Gly Gln Gly Leu Gly Phe Asp Ala Ala
        435                 440                 445

Ile Ala Tyr Ala Leu Arg Glu Gln Pro Pro Ser Thr Ser Gly Pro Thr
    450                 455                 460

Ala Gly Gly Ser Thr Arg Leu Thr Lys Arg Glu Arg Gln Val Ala Gly
465                 470                 475                 480

Leu Ile Ala Glu Gly Leu Thr Asn Gln Ala Ile Ala Asp Arg Leu Val
                485                 490                 495

Ile Ser Pro Arg Thr Ala Gln Gly His Val Glu His Ile Leu Ala Lys
            500                 505                 510

Leu Gly Phe Thr Ser Arg Ala Gln Val Ala Ala Trp Val Val Glu Arg
        515                 520                 525

Thr Asp Asp Glx
    530

<210> SEQ ID NO 4
<211> LENGTH: 1203
<212> TYPE: DNA
<213> ORGANISM: Rhodococcus erythropolis HL PM-1

<400> SEQUENCE: 4
atggggttca ccggaaatgt cgaggcgctg tcgggaatcc gagtggtcga cgccgcgacg      60
atggtcgccg gccccttggg tgcgtcgctg ctcgccgatt cggtgccga cgtcatcaag     120 gtcgagccga tcgcggcga cgagtcgcgg acgttcgggc cgggacgaga cggcatgagt     180
ggtgtctatt ccggcgtgaa ccgaaacaag cgcgccctcg cgctcgacct tcggacggag     240
gcgggccgtg acctgttcca cgagctgtgc tcgacagcgg acgtgctcat cgagaacatg     300
ctgccggcgg tacgggaacg attcgggctg actgccgccg agcttcgcga acggcaccct     360
cacctgatct gcctcaatgt cagcgggtac ggcgagaccg gccccctcgc gggtcgcccc     420
gcaatggacc cggtggctca ggcgctcacc ggactcatgc aggcgaccgg tgagcgctcg     480
gggaggtcgc tcaaggccgg tccgcccgtc gccgacagtg cggcgggcta cctggtcgcg     540
atcgccgccc tcgtcgcgct cttcgcgaaa cagcgcacgg ggagggggca aagtggctcg     600
gtgtccctgg tgggggcgct gttccatttg cagacgccgt ggctggggca gtacctcctg     660
gccgactaca tccagggcaa ggtgggcaac ggcagcaatt tctacgcgcc gtacaacgcc     720
tatacgaccc gtgacggcgg cgcggtgcat gtcgttgcct tcaacgaccg ccacttcgtc     780
aagctcgccc gggcgatggg tgccgaggct ctgatcgaca tccgcgcttg cgcgcaggcc     840
gcatcccgac tggagaaccg tgaggccctc gacgacgccg tcgcaccctg gttcgccgac     900
cgcgaccggg acgacgtggt tgcactgctc tcggcccacg acatcatctg tgccccgatt     960
ctcgcgtacg acgaggccgt caggcatccc cagatccagg cactggacct cgtcgtcgac    1020
atcacccacg acgaactcgg accgctgcag gttccgggtc tcccggtcaa gctctcgggc    1080
accccgggac acgtacaccg cccaccgacg tcgttgggcg agcacaccac cgagattctc    1140
```

```
                                 agcgatctcg gctacaagga cgaccggatt gcggccctcc gggccgaacg ggtcgtccga   1200
tga                                                                 1203
```

<210> SEQ ID NO 5
<211> LENGTH: 401
<212> TYPE: PRT
<213> ORGANISM: Rhodococcus erythropolis HL PM-1

<400> SEQUENCE: 5

```
Met Gly Phe Thr Gly Asn Val Glu Ala Leu Ser Gly Ile Arg Val Val
 1               5                  10                  15

Asp Ala Ala Thr Met Val Ala Gly Pro Leu Gly Ala Ser Leu Leu Ala
                20                  25                  30

Asp Phe Gly Ala Asp Val Ile Lys Val Glu Pro Ile Gly Gly Asp Glu
            35                  40                  45

Ser Arg Thr Phe Gly Pro Gly Arg Asp Gly Met Ser Gly Val Tyr Ser
        50                  55                  60

Gly Val Asn Arg Asn Lys Arg Ala Leu Ala Leu Asp Leu Arg Thr Glu
 65                  70                  75                  80

Ala Gly Arg Asp Leu Phe His Glu Leu Cys Ser Thr Ala Asp Val Leu
                85                  90                  95

Ile Glu Asn Met Leu Pro Ala Val Arg Glu Arg Phe Gly Leu Thr Ala
            100                 105                 110

Ala Glu Leu Arg Glu Arg His Pro His Leu Ile Cys Leu Asn Val Ser
        115                 120                 125

Gly Tyr Gly Glu Thr Gly Pro Leu Ala Gly Arg Pro Ala Met Asp Pro
130                 135                 140

Val Ala Gln Ala Leu Thr Gly Leu Met Gln Ala Thr Gly Glu Arg Ser
145                 150                 155                 160

Gly Arg Ser Leu Lys Ala Gly Pro Pro Val Ala Asp Ser Ala Ala Gly
                165                 170                 175

Tyr Leu Val Ala Ile Ala Ala Leu Val Ala Leu Phe Ala Lys Gln Arg
            180                 185                 190

Thr Gly Glu Gly Gln Ser Gly Ser Val Ser Leu Val Gly Ala Leu Phe
        195                 200                 205

His Leu Gln Thr Pro Trp Leu Gly Gln Tyr Leu Leu Ala Asp Tyr Ile
    210                 215                 220

Gln Gly Lys Val Gly Asn Gly Ser Asn Phe Tyr Ala Pro Tyr Asn Ala
225                 230                 235                 240

Tyr Thr Thr Arg Asp Gly Gly Ala Val His Val Ala Phe Asn Asp
                245                 250                 255

Arg His Phe Val Lys Leu Ala Arg Ala Met Gly Ala Glu Ala Leu Ile
            260                 265                 270

Asp Asp Pro Arg Phe Ala Gln Ala Ala Ser Arg Leu Glu Asn Arg Glu
        275                 280                 285

Ala Leu Asp Asp Ala Val Ala Pro Trp Phe Ala Asp Arg Asp Arg Asp
    290                 295                 300

Asp Val Val Ala Leu Leu Ser Ala His Asp Ile Ile Cys Ala Pro Ile
305                 310                 315                 320

Leu Ala Tyr Asp Glu Ala Val Arg His Pro Gln Ile Gln Ala Leu Asp
                325                 330                 335

Leu Val Val Asp Ile Thr His Asp Glu Leu Gly Pro Leu Gln Val Pro
            340                 345                 350

Gly Leu Pro Val Lys Leu Ser Gly Thr Pro Gly His Val His Arg Pro
```

```
            355              360                365
Pro Thr Ser Leu Gly Glu His Thr Thr Glu Ile Leu Ser Asp Leu Gly
        370                 375                380

Tyr Lys Asp Asp Arg Ile Ala Ala Leu Arg Ala Glu Arg Val Val Arg
385                 390                 395                 400

Glx
401

<210> SEQ ID NO 6
<211> LENGTH: 888
<212> TYPE: DNA
<213> ORGANISM: Rhodococcus erythropolis HL PM-1

<400> SEQUENCE: 6
atgaaggtcg gaatcaggat cccgggagca ggaccgtggg cagggcccga ggcgatcacg      60
gaggtgtcgc ggttcgctga aagatcggc ttcgactcgc tctggatgac tgatcatgtg     120
gccttgccga cccgagtcga cggcgtac ccgtacaccg acgacggcaa gttcctgtgg      180
gatccggcca cgccgtacct cgactgcctc acgtcgttga cgtgggcggc ggccgcgacc    240
gagcggatgg agctcggcac gtcgtgcctc atcctgccgt ggcgtccgct cgtccagacc    300
gccaagacac tggtgagcat cgacgtgatg tcgcgcggcc ggctgtcggt cgccatcggc    360
gtgggctgga tgaaggagca gttcgagctg ctgggagcgc ttttcaagga ccgggggaag    420
cggaccacgg agatggtcaa cgcgatgcgg cacatgtgga aggaagacga ggtcgccttc    480
gacggtgagt tctaccaact ccacgacttc aagatgtatc gaagccggt gcggggcacg     540 atccccgtct ggttcgcggg atacagcacc gcctccctgc cgtatcgc cgccatcggc      600 gacgggtggc acccattggc gatcgggccg gaggagtacg ccggctacct ggccaccctg    660
aagcaatacg ccgaggaagc cggccgcgac atgaacgaaa tcaccctcac cgcgcggcct    720
ctgcggaagg cgccgtacaa cgccgagacg atcgaagcgt acggcgaact cggtgtcacc    780
cacttcatct gcgacacgtc gttcgagcac gacacccctcg aagcaaccat ggacgagctc    840
gccgagcttg ccgacgccgt cctccccacc gcacacaacc tgccctga                 888

<210> SEQ ID NO 7
<211> LENGTH: 296
<212> TYPE: PRT
<213> ORGANISM: Rhodococcus erythropolis HL PM-1

<400> SEQUENCE: 7

Met Lys Val Gly Ile Arg Ile Pro Gly Ala Gly Pro Trp Ala Gly Pro
  1               5                  10                  15

Glu Ala Ile Thr Glu Val Ser Arg Phe Ala Glu Lys Ile Gly Phe Asp
                20                  25                  30

Ser Leu Trp Met Thr Asp His Val Ala Leu Pro Thr Arg Val Glu Thr
            35                  40                  45

Ala Tyr Pro Tyr Thr Asp Asp Gly Lys Phe Leu Trp Asp Pro Ala Thr
        50                  55                  60

Pro Tyr Leu Asp Cys Leu Thr Ser Leu Thr Trp Ala Ala Ala Thr
65                  70                  75                  80

Glu Arg Met Glu Leu Gly Thr Ser Cys Leu Ile Leu Pro Trp Arg Pro
                85                  90                  95

Leu Val Gln Thr Ala Lys Thr Leu Val Ser Ile Asp Val Met Ser Arg
                100                 105                 110

Gly Arg Leu Ser Val Ala Ile Gly Val Gly Trp Met Lys Glu Gln Phe
```

```
        115                 120                     125
Glu Leu Leu Gly Ala Pro Phe Lys Asp Arg Gly Lys Arg Thr Thr Glu
    130                 135                 140

Met Val Asn Ala Met Arg His Met Trp Lys Glu Asp Val Ala Phe
145                 150                 155                 160

Asp Gly Glu Phe Tyr Gln Leu His Asp Phe Lys Met Tyr Pro Lys Pro
                165                 170                 175

Val Arg Gly Thr Ile Pro Val Trp Phe Ala Gly Tyr Ser Thr Ala Ser
            180                 185                 190

Leu Arg Arg Ile Ala Ala Ile Gly Asp Gly Trp His Pro Leu Ala Ile
        195                 200                 205

Gly Pro Glu Glu Tyr Ala Gly Tyr Leu Ala Thr Leu Lys Gln Tyr Ala
    210                 215                 220

Glu Glu Ala Gly Arg Asp Met Asn Glu Ile Thr Leu Thr Ala Arg Pro
225                 230                 235                 240

Leu Arg Lys Ala Pro Tyr Asn Ala Glu Thr Ile Glu Ala Tyr Gly Glu
                245                 250                 255

Leu Gly Val Thr His Phe Ile Cys Asp Thr Ser Phe Glu His Asp Thr
            260                 265                 270

Leu Glu Ala Thr Met Asp Glu Leu Ala Glu Leu Ala Asp Ala Val Leu
        275                 280                 285

Pro Thr Ala His Asn Leu Pro Glx
    290                 295

<210> SEQ ID NO 8
<211> LENGTH: 1455
<212> TYPE: DNA
<213> ORGANISM: Rhodococcus erythropolis HL PM-1

<400> SEQUENCE: 8
gtgcaggcac tcacctcatc ggttcccctcgtcatcggcg accaactgac cccatcgtcg      60
acggggcga ccttcgactc gatcaaccccg gccgacgggt cgcacctggc cagcgtcgcc    120
gaggccacgg ccgcggacgt cgcgcgtgcg gtcgaagccg cgaaggcggc ggccaggacg    180
tggcagcgca tgcgcccggc ccagcgaacc cgcctgatgt tccgctacgc cgcgctgatc    240
gaggaacaca agaccgagct cgcccagctg cagagtcggg acatgggcaa gcccatccgc    300
gagtcgctcg ggatcgacct gccgatcatg atcgagacgc tcgagtactt cgcgggcctc    360
gtgaccaaga tcgagggccg aacgacgccg gcgcccggcc gtttcctcaa ctacaccctg    420
cgtgagccga tcggtgtggt gggcgccatc actccctgga attttcctgc agtgcaggcg    480
gtctggaaga tcgcccccggc tcttgcgatg gcaacgcca tcgtgctgaa gcctgcgcag    540
ctcgcaccac tcgtgcccgt ggcactcggg gagctcgccc tcgaggcggg tctgccgccc    600
gggctggtca acgtcctgcc cggccgcggg tcggtagcgg gtaacgcctt ggtgcagcac    660
ccatcggtcg gcaaggtgac gttcaccggc tcgaccgagg tcggccagca gatcggccgg    720
atggcggcca ccgcctcat acgcgcttcg ctggagctgg gcgaaagtc tgcgctcgtg    780
gcgttcggcg actcgtcccc gaaggcggtc gcagccgtgg tcttccaggc gatgtacagc    840
aaccagggtg agacctgcac ggcgccgagc aggttgctcg tcgagcggcc gatctacgac    900
gaggtggtcg agctcgtcca ggcacgtgtc gaggccgccc gggtgggcga cccgctcgac    960
cccgacacgg agatcggccc gttgatcagt gccgagcagc gggagtcggt ccactcgtac   1020
gtcgtctccg ggaccgagga aggcgccacg ctgatcagcg gtggcgacca gtcgccgacc   1080
```

-continued

```
ggagcgccgg agcagggatt ctactaccgt ccgacgctct tctccggagt caccgcggac    1140
atgcgcatcg ctcgggagga gatcttcgga cccgtgctgt cggtgctgcc gttcgaggga    1200
gaagaggagg cgatcaccct ggccaacgac accgtcttcg gctggccgc gggcgtcttc    1260 acccgcgatg tgggccgcgc actgcggttc gcgcagacgc tcgacgccgg caacgtgtgg    1320
atcaacagct ggggagtgct caacccggcg tcgccgtatc gaggcttcgg gcagagcggc    1380
tacggcagcg acctcggcca ggcggccatc gaaagcttca ccaaggagaa gagcatatgg    1440
gcacgcctgg actga                                                    1455
```

<210> SEQ ID NO 9
<211> LENGTH: 485
<212> TYPE: PRT
<213> ORGANISM: Rhodococcus erythropolis HL PM-1

<400> SEQUENCE: 9

```
Val Gln Ala Leu Thr Ser Ser Val Pro Leu Val Ile Gly Asp Gln Leu
 1               5                  10                  15

Thr Pro Ser Ser Thr Gly Ala Thr Phe Asp Ser Ile Asn Pro Ala Asp
            20                  25                  30

Gly Ser His Leu Ala Ser Val Ala Glu Ala Thr Ala Ala Asp Val Ala
        35                  40                  45

Arg Ala Val Glu Ala Ala Lys Ala Ala Ala Arg Thr Trp Gln Arg Met
    50                  55                  60

Arg Pro Ala Gln Arg Thr Arg Leu Met Phe Arg Tyr Ala Ala Leu Ile
65                  70                  75                  80

Glu Glu His Lys Thr Glu Leu Ala Gln Leu Gln Ser Arg Asp Met Gly
                85                  90                  95

Lys Pro Ile Arg Glu Ser Leu Gly Ile Asp Leu Pro Ile Met Ile Glu
            100                 105                 110

Thr Leu Glu Tyr Phe Ala Gly Leu Val Thr Lys Ile Glu Gly Arg Thr
        115                 120                 125

Thr Pro Ala Pro Gly Arg Phe Leu Asn Tyr Thr Leu Arg Glu Pro Ile
    130                 135                 140

Gly Val Val Gly Ala Ile Thr Pro Trp Asn Phe Pro Ala Val Gln Ala
145                 150                 155                 160

Val Trp Lys Ile Ala Pro Ala Leu Ala Met Gly Asn Ala Ile Val Leu
                165                 170                 175

Lys Pro Ala Gln Leu Ala Pro Leu Val Pro Val Ala Leu Gly Glu Leu
            180                 185                 190

Ala Leu Glu Ala Gly Leu Pro Pro Gly Leu Val Asn Val Leu Pro Gly
        195                 200                 205

Arg Gly Ser Val Ala Gly Asn Ala Leu Val Gln His Pro Ser Val Gly
    210                 215                 220

Lys Val Thr Phe Thr Gly Ser Thr Glu Val Gly Gln Gln Ile Gly Arg
225                 230                 235                 240

Met ala Ala Asp Arg Leu Ile Thr Ala Ser Leu Glu Leu Gly Gly Lys
                245                 250                 255

Ser Ala Leu Val Ala Phe Gly Asp Ser Ser Pro Lys Ala Val Ala Ala
            260                 265                 270

Val Val Phe Gln Ala Met Tyr Ser Asn Gln Gly Glu Thr Cys Thr Ala
        275                 280                 285

Pro Ser Arg Leu Leu Val Glu Arg Pro Ile Tyr Asp Glu Val Val Glu
    290                 295                 300
```

```
Leu Val Gln Ala Arg Val Glu Ala Ala Arg Val Gly Asp Pro Leu Asp
305                 310                 315                 320

Pro Asp Thr Glu Ile Gly Pro Leu Ile Ser Ala Glu Gln Arg Glu Ser
                325                 330                 335

Val His Ser Tyr Val Val Ser Gly Thr Glu Gly Ala Thr Leu Ile
                340                 345                 350

Ser Gly Gly Asp Gln Ser Pro Thr Gly Ala Pro Glu Gln Gly Phe Tyr
                355                 360                 365

Tyr Arg Pro Thr Leu Phe Ser Gly Val Thr Ala Asp Met Arg Ile Ala
                370                 375                 380

Arg Glu Glu Ile Phe Gly Pro Val Leu Ser Val Leu Pro Phe Glu Gly
385                 390                 395                 400

Glu Glu Glu Ala Ile Thr Leu Ala Asn Asp Thr Val Phe Gly Leu Ala
                405                 410                 415

Ala Gly Val Phe Thr Arg Asp Val Gly Arg Ala Leu Arg Phe Ala Gln
                420                 425                 430

Thr Leu Asp Ala Gly Asn Val Trp Ile Asn Ser Trp Gly Val Leu Asn
                435                 440                 445

Pro Ala Ser Pro Tyr Arg Gly Phe Gly Gln Ser Gly Tyr Gly Ser Asp
450                 455                 460

Leu Gly Gln Ala Ala Ile Glu Ser Phe Thr Lys Glu Lys Ser Ile Trp
465                 470                 475                 480

Ala Arg Leu Asp Glx
                485

<210> SEQ ID NO 10
<211> LENGTH: 1611
<212> TYPE: DNA
<213> ORGANISM: Rhodococcus erythropolis HL PM-1

<400> SEQUENCE: 10
atgggcacgc tggactgac ctccgggaca tcgaggtcac ggaccatcag gcggttgatc      60
gacgcccgcc acacccagga ttggaagcca gcggcggact acacgatcac cgaggacgcc     120
ctcttctcac gcgaccccga cgccgtggcc gtgctgcgcg gggggctcca cacgcccgag     180
aaggtgacgt tcggtcaggt acagcacgcc gctgtgcgcg tcgccggtgt cctccggtcc     240
cgcggggtcg agcccggtga ccgcgtggtc ctgtacctcg acccctcggt ggaggccgcc     300
gaggtcgtct tcgggtgct cgtcgccggc cgtgctcg tgcccgtccc gcgactgctc        360
accggtacct cggtggcgca ccggctcgcc gactcgggcg cgactgtgct ggtcacggac     420
ggtccgggcg tcgaccggct ggagtcgaca ggatgttccc tgcacgacgt cgacgtgctc     480
acggtggacg gcgcccacgg cgcgccgctc ggggacctga cccgccgggt cgaccccgctc    540 gccccggtgc cgcggcggtc ctcggatctt gctctgctga tgtacacgtc gggcaccagc    600
ggcccgccca aggcatcgt tcacggccat cgggtcctgc tcggacatgc gggggtcgac     660
tacgccttcg aactgttcag gccgggtgac gtctatttcg gcactgcgga ctggggtgg    720 atcggcggcc tgatgctcgg gttgctggtt ccgtggtctc tcggcgttcc tgtcgtggct    780
caccggccgc agcgtttcga tccggcgcc accctggaca tgctgagccg gtacagcgtg    840
acgaccgcct tcctgccggc gtcggttctt cggatgtttg ccgaacacgg ggaaccggcc    900
cagcggcgtc tgcgggcggt ggtgaccgga ggcgagcccg ccggcgcggt ggaactcggc    960
tgggcccggc ggcatctcag cgacgccgtc aacaaggcct acgtcagac cgaggccaac    1020 gcgctcatcg cgactccgc tgttctcgga tccgtcgacg acgcgaccat gggcgctccg    1080
```

-continued

```
tatcccgggc accgcatcgc gctcctggac gacgcgggca ctcacgtcgc gcccggtgag    1140
gtcggtgaga ttgcgctgga acttccggat tcggttgcgc tgctcggcta ttgggatgcg    1200
tcgtcggcta gtgtggtacc tcccgccggg agttggcacc ggacaggcga cctggcacgg    1260
ctcgcacatg gacgccggct ggagtacctc ggccgcgccg acgacgtgat caagagccgc    1320
ggctaccgca tcgtccggc ggagatcgaa gaggcactga agcgtcaccc ccaggtcctg     1380
gacgcggcgg cggtagggct gcccgacccg gagtcggggc agcaggtcaa ggcattcgtc    1440
cacctcgctg ccgcgaact caccgaggag atttcggcgg aactccgtga actcgtcgcc     1500
gccgcggtcg gcccacacgc acgcccccgc gagatagagg cagtcgcagc gttgccgcgc    1560
acggagaccg gaaaggtccg gcggcgggaa ctggtgccgc cctcggctta g             1611
```

<210> SEQ ID NO 11
<211> LENGTH: 537
<212> TYPE: PRT
<213> ORGANISM: Rhodococcus erythropolis HL PM-1

<400> SEQUENCE: 11

```
Met Gly Thr Pro Gly Leu Thr Ser Gly Thr Ser Arg Ser Arg Thr Ile
 1               5                  10                  15

Arg Arg Leu Ile Asp Ala Arg His Thr Gln Asp Trp Lys Pro Ala Ala
            20                  25                  30

Asp Tyr Thr Ile Thr Glu Asp Ala Leu Phe Ser Arg Asp Pro Asp Ala
        35                  40                  45

Val Ala Val Leu Arg Gly Gly Leu His Thr Pro Glu Lys Val Thr Phe
    50                  55                  60

Gly Gln Val Gln His Ala Ala Val Arg Val Ala Gly Val Leu Arg Ser
65                  70                  75                  80

Arg Gly Val Glu Pro Gly Asp Arg Val Val Leu Tyr Leu Asp Pro Ser
                85                  90                  95

Val Glu Ala Ala Glu Val Val Phe Gly Val Leu Val Ala Gly Ala Val
            100                 105                 110

Leu Val Pro Val Pro Arg Leu Leu Thr Gly Thr Ser Val Ala His Arg
        115                 120                 125

Leu Ala Asp Ser Gly Ala Thr Val Leu Val Thr Asp Gly Pro Gly Val
    130                 135                 140

Asp Arg Leu Glu Ser Thr Gly Cys Ser Leu His Asp Val Asp Val Leu
145                 150                 155                 160

Thr Val Asp Gly Ala His Gly Ala Pro Leu Gly Asp Leu Thr Arg Arg
                165                 170                 175

Val Asp Pro Leu Ala Pro Val Pro Arg Arg Ser Ser Asp Leu Ala Leu
            180                 185                 190

Leu Met Tyr Thr Ser Gly Thr Ser Gly Pro Pro Lys Gly Ile Val His
        195                 200                 205

Gly His Arg Val Leu Leu Gly His Ala Gly Val Asp Tyr Ala Phe Glu
    210                 215                 220

Leu Phe Arg Pro Gly Asp Val Tyr Phe Gly Thr Ala Asp Trp Gly Trp
225                 230                 235                 240

Ile Gly Gly Leu Met Leu Gly Leu Leu Val Pro Trp Ser Leu Gly Val
                245                 250                 255

Pro Val Val Ala His Arg Pro Gln Arg Phe Asp Pro Gly Ala Thr Leu
            260                 265                 270

Asp Met Leu Ser Arg Tyr Ser Val Thr Thr Ala Phe Leu Pro Ala Ser
```

```
                    275                 280                 285
Val Leu Arg Met Phe Ala Glu His Gly Glu Pro Ala Gln Arg Leu
        290                 295                 300

Arg Ala Val Val Thr Gly Gly Glu Pro Ala Gly Ala Val Glu Leu Gly
305                 310                 315                 320

Trp Ala Arg Arg His Leu Ser Asp Ala Val Asn Lys Ala Tyr Gly Gln
                325                 330                 335

Thr Glu Ala Asn Ala Leu Ile Gly Asp Ser Ala Val Leu Gly Ser Val
            340                 345                 350

Asp Asp Ala Thr Met Gly Ala Pro Tyr Pro Gly His Arg Ile Ala Leu
            355                 360                 365

Leu Asp Asp Ala Gly Thr His Val Ala Pro Gly Glu Val Gly Glu Ile
370                 375                 380

Ala Leu Glu Leu Pro Asp Ser Val Ala Leu Leu Gly Tyr Trp Asp Ala
385                 390                 395                 400

Ser Ser Ala Ser Val Val Pro Pro Ala Gly Ser Trp His Arg Thr Gly
                405                 410                 415

Asp Leu Ala Arg Leu Ala His Gly Arg Arg Leu Glu Tyr Leu Gly Arg
            420                 425                 430

Ala Asp Asp Val Ile Lys Ser Arg Gly Tyr Arg Ile Gly Pro Ala Glu
            435                 440                 445

Ile Glu Glu Ala Leu Lys Arg His Pro Gln Val Leu Asp Ala Ala Ala
450                 455                 460

Val Gly Leu Pro Asp Pro Glu Ser Gly Gln Gln Val Lys Ala Phe Val
465                 470                 475                 480

His Leu Ala Ala Gly Glu Leu Thr Glu Glu Ile Ser Ala Glu Leu Arg
                485                 490                 495

Glu Leu Val Ala Ala Ala Val Gly Pro His Ala Arg Pro Arg Glu Ile
            500                 505                 510

Glu Ala Val Ala Ala Leu Pro Arg Thr Glu Thr Gly Lys Val Arg Arg
            515                 520                 525

Arg Glu Leu Val Pro Pro Ser Ala Glx
        530                 535

<210> SEQ ID NO 12
<211> LENGTH: 525
<212> TYPE: DNA
<213> ORGANISM: Rhodococcus erythropolis HL PM-1

<400> SEQUENCE: 12
gtggagcgcc atccacccac ccgaacacag aagtgcaaga agaaggacga agcaatgcga      60
aagttctggc acgtcggcat caatgtgacc gacatggaca atcgatcga cttctatcgg     120 cgaatcggtt tcgaggtagt gcaggatcgg gaggtggagg acagcaacct tgcgcgggca     180
ttcatggtcg agggtgccag caagctccgc ttcgcacact tgcgcctgaa cgactcccg      240 gacgaggcga tgctggacct catcgagtgg agggacgcac gttccgaggg gcgagcgcag     300
agcgacctcg tgcacccggg actctgccga ttctcgatcc tcaccgacga catcgacgcc     360
gagtatgcac ggctggcgga cgacggcgtc cagttcctgc acgcgccgca gacgatcatg     420
ggtccggacg gcgtcaaggg ctggcggctg ctcttcgcgc gcgatcccga cggcacgctg     480
ttccatttcg ccgaacttgt ggggcaggcc gctacggtca gctga                    525

<210> SEQ ID NO 13
<211> LENGTH: 175
```

```
<212> TYPE: PRT
<213> ORGANISM: Rhodococcus erythropolis HL PM-1

<400> SEQUENCE: 13

Val Glu Arg His Pro Pro Thr Arg Thr Gln Lys Cys Lys Lys Lys Asp
  1               5                  10                  15

Glu Ala Met Arg Lys Phe Trp His Val Gly Ile Asn Val Thr Asp Met
             20                  25                  30

Asp Lys Ser Ile Asp Phe Tyr Arg Arg Ile Gly Phe Glu Val Val Gln
         35                  40                  45

Asp Arg Glu Val Glu Asp Ser Asn Leu Ala Arg Ala Phe Met Val Glu
     50                  55                  60

Gly Ala Ser Lys Leu Arg Phe Ala His Leu Arg Leu Asn Asp Ser Pro
 65                  70                  75                  80

Asp Glu Ala Met Leu Asp Leu Ile Glu Trp Arg Asp Ala Arg Ser Glu
                 85                  90                  95

Gly Arg Ala Gln Ser Asp Leu Val His Pro Gly Leu Cys Arg Phe Ser
            100                 105                 110

Ile Leu Thr Asp Asp Ile Asp Ala Glu Tyr Ala Arg Leu Ala Asp Asp
        115                 120                 125

Gly Val Gln Phe Leu His Ala Pro Gln Thr Ile Met Gly Pro Asp Gly
    130                 135                 140

Val Lys Gly Trp Arg Leu Leu Phe Ala Arg Asp Pro Asp Gly Thr Leu
145                 150                 155                 160

Phe His Phe Ala Glu Leu Val Gly Gln Ala Ala Thr Val Ser Glx
                165                 170                 175

<210> SEQ ID NO 14
<211> LENGTH: 810
<212> TYPE: DNA
<213> ORGANISM: Rhodococcus erythropolis HL PM-1

<400> SEQUENCE: 14
gtcccgggaa gcagcgcgac tgacgagcgg ggcgagcaat ccagcgagca gctggtgccc      60
gccatctcgc gcgcaacccg cgtactcgag acactggtcc agcagtccac cggagccaca     120
ctcaccgagt tggccaagcg gtgcgctctg gcgaagagca cggcatcggt cctgctccgg     180
accatggtgg tcgagggcct cgtcgtgtac gaccaggaga cgcgccggta caacctcggc     240
ccgctgctcg tggagttcgg cgtggctgcg atcgcgcgaa catcggcggt cgccgcgtcg     300
cggacgtaca tggagtggtt ggccgagcgg accgagctgg catgtctcgc catccagccg     360
atgccggacg tcacttcac ggcgatcgcg aagatcgaga ccgcaaggc cgtcaaggtc     420 accatcgagg tcggctctcg cttcggtcga dacactccgt tgatcagccg actcgcggcg     480
gcatggccga gcaggggtcg cccggagctt gtcgagtacc ccgccgatga gctcgacgag     540
ctccgggcgc agggctacgg cgctgtctat ggcgaatatc gaccggaact caacgtcgtg     600
ggggtcccgg tgttcgaccg agacggcgag ccgtgtctgt tcatcgccct gctcggtatc     660
ggcgacgatc tcacagccga cggtgtggcc gggatcgccg actacctcgt cacggtttcg     720
cgggagatca gctcgcatat cggcggccgc attccggcgg actacccgac tcctgtcggg     780
gcccccgacc tcggcgccgg gcgcggctga                                     810

<210> SEQ ID NO 15
<211> LENGTH: 270
<212> TYPE: PRT
<213> ORGANISM: Rhodococcus erythropolis HL PM-1
```

<400> SEQUENCE: 15

| | | | | | | | | | | | | | | | |
|---|---|---|---|---|---|---|---|---|---|---|---|---|---|---|---|
|Val|Pro|Gly|Ser|Ser|Ala|Thr|Asp|Glu|Arg|Gly|Glu|Gln|Ser|Glu|
|1| | | |5| | | | |10| | | | |15|
|Gln|Leu|Val|Pro|Ala|Ile|Ser|Arg|Ala|Thr|Arg|Val|Leu|Glu|Thr|Leu|
| | | |20| | | | |25| | | | |30| | |
|Val|Gln|Gln|Ser|Thr|Gly|Ala|Thr|Leu|Thr|Glu|Leu|Ala|Lys|Arg|Cys|
| | |35| | | | |40| | | | |45| | | |
|Ala|Leu|Ala|Lys|Ser|Thr|Ala|Ser|Val|Leu|Leu|Arg|Thr|Met|Val|Val|
| |50| | | | |55| | | | |60| | | | |
|Glu|Gly|Leu|Val|Val|Tyr|Asp|Gln|Glu|Thr|Arg|Arg|Tyr|Asn|Leu|Gly|
|65| | | | |70| | | | |75| | | | |80|
|Pro|Leu|Leu|Val|Glu|Phe|Gly|Val|Ala|Ala|Ile|Ala|Arg|Thr|Ser|Ala|
| | | | |85| | | | |90| | | | |95| |
|Val|Ala|Ala|Ser|Arg|Thr|Tyr|Met|Glu|Trp|Leu|Ala|Glu|Arg|Thr|Glu|
| | | |100| | | | |105| | | | |110| | |
|Leu|Ala|Cys|Leu|Ala|Ile|Gln|Pro|Met|Pro|Asp|Gly|His|Phe|Thr|Ala|
| | |115| | | | |120| | | | |125| | | |
|Ile|Ala|Lys|Ile|Glu|Ser|Arg|Lys|Ala|Val|Lys|Val|Thr|Ile|Glu|Val|
| |130| | | | |135| | | | |140| | | | |
|Gly|Ser|Arg|Phe|Gly|Arg|Asp|Thr|Pro|Leu|Ile|Ser|Arg|Leu|Ala|Ala|
|145| | | | |150| | | | |155| | | | |160|
|Ala|Trp|Pro|Ser|Arg|Gly|Arg|Pro|Glu|Leu|Val|Glu|Tyr|Pro|Ala|Asp|
| | | | |165| | | | |170| | | | |175| |
|Glu|Leu|Asp|Glu|Leu|Arg|Ala|Gln|Gly|Tyr|Gly|Ala|Val|Tyr|Gly|Glu|
| | | |180| | | | |185| | | | |190| | |
|Tyr|Arg|Pro|Glu|Leu|Asn|Val|Val|Gly|Val|Pro|Val|Phe|Asp|Arg|Asp|
| | |195| | | | |200| | | | |205| | | |
|Gly|Glu|Pro|Cys|Leu|Phe|Ile|Ala|Leu|Leu|Gly|Ile|Gly|Asp|Asp|Leu|
| |210| | | | |215| | | | |220| | | | |
|Thr|Ala|Asp|Gly|Val|Ala|Gly|Ile|Ala|Asp|Tyr|Leu|Val|Thr|Val|Ser|
|225| | | | |230| | | | |235| | | | |240|
|Arg|Glu|Ile|Ser|Ser|His|Ile|Gly|Gly|Arg|Ile|Pro|Ala|Asp|Tyr|Pro|
| | | | |245| | | | |250| | | | |255| |
|Thr|Pro|Val|Gly|Ala|Pro|Asp|Leu|Gly|Ala|Gly|Arg|Gly|Glx|
| | | |260| | | | |265| | | | |270| |

<210> SEQ ID NO 16
<211> LENGTH: 681
<212> TYPE: DNA
<213> ORGANISM: Rhodococcus erythropolis HL PM-1

<400> SEQUENCE: 16

```
atgaagagca gcaagatcgc cgtcgtcggc ggcaccggac cccagggaaa ggggctggcc      60
taccggttcg cggcggccgg ctggcctgtc gtcatcggat cgcgttctgc cgaacgcgcg     120
gaggaggcgg ccctcgaggt gcgcagacgc gccggtgacg cgccgtggt cagcgccgcc     180
gacaatgcgt cggcagctgc cgactgtccc atcatcctgc tggtcgtccc atacgacggc     240
catcgtgagc tggtttcgga actggcaccc atcttcgcgg caagctcgt cgtcagctgc     300
gtgaatccgc tcggcttcga caagtccggg gcctacggtt tggacgtcga ggaagggagc     360
gccgccgagc aactgcgcga cctcgtgccc ggtgccacgg tggtcgctgc ctttcaccat     420
ctgtcggcgg tcaacctctg ggaacatgag ggccccttc ccgaggatgt gctcgtgtgc     480
ggcgacgatc ggtccgcgaa ggacgaggtg gctcggctcg cagtcgcgat caccggccgg     540
```

```
ccgggcatcg acggagggc gctgcggtg gcgcggcagc tcgaaccgtt gaccgccgtt       600
ctcatcaatg tcaaccggcg ctacaagacg ctctccggtc tcgccgtgaa cggggttgtt       660
catgatccac gagctgcgtg a                                                  681
```

<210> SEQ ID NO 17
<211> LENGTH: 227
<212> TYPE: PRT
<213> ORGANISM: Rhodococcus erythropolis HL PM-1

<400> SEQUENCE: 17

```
Met Lys Ser Ser Lys Ile Ala Val Val Gly Thr Gly Pro Gln Gly
 1               5                  10                  15

Lys Gly Leu Ala Tyr Arg Phe Ala Ala Ala Gly Trp Pro Val Val Ile
                20                  25                  30

Gly Ser Arg Ser Ala Glu Arg Ala Glu Glu Ala Ala Leu Glu Val Arg
            35                  40                  45

Arg Arg Ala Gly Asp Gly Ala Val Val Ser Ala Ala Asp Asn Ala Ser
        50                  55                  60

Ala Ala Ala Asp Cys Pro Ile Ile Leu Leu Val Val Pro Tyr Asp Gly
 65                  70                  75                  80

His Arg Glu Leu Val Ser Glu Leu Ala Pro Ile Phe Ala Gly Lys Leu
                85                  90                  95

Val Val Ser Cys Val Asn Pro Leu Gly Phe Asp Lys Ser Gly Ala Tyr
            100                 105                 110

Gly Leu Asp Val Glu Glu Gly Ser Ala Ala Glu Gln Leu Arg Asp Leu
        115                 120                 125

Val Pro Gly Ala Thr Val Val Ala Ala Phe His His Leu Ser Ala Val
    130                 135                 140

Asn Leu Trp Glu His Glu Gly Pro Leu Pro Glu Asp Val Leu Val Cys
145                 150                 155                 160

Gly Asp Asp Arg Ser Ala Lys Asp Glu Val Ala Arg Leu Ala Val Ala
                165                 170                 175

Ile Thr Gly Arg Pro Gly Ile Asp Gly Gly Ala Leu Arg Val Ala Arg
            180                 185                 190

Gln Leu Glu Pro Leu Thr Ala Val Leu Ile Asn Val Asn Arg Arg Tyr
        195                 200                 205

Lys Thr Leu Ser Gly Leu Ala Val Asn Gly Val Val His Asp Pro Arg
    210                 215                 220

Ala Ala Glx
225
```

<210> SEQ ID NO 18
<211> LENGTH: 318
<212> TYPE: DNA
<213> ORGANISM: Rhodococcus erythropolis HL PM-1

<400> SEQUENCE: 18

```
atgatccacg agctgcgtga gtaccttgcg ctgccgggcc gtgccgagga cctgcaccgc       60
aggttcgccg acgacacgct ggccctgttc gcggaattcg ggctgcaggt cgagggcttc      120
tggcacgagg caggcaaccg tgcccggatc gtgtacctgt tggcgttccc cgacttcgag      180
gccgcggacg cgcattgggc ccggttccag gccgaccccc gtggtgtgc gttgaaggca      240 cgcaccgaga gcgacgggcc gctcatctcg gagatccgga gcacgttcct gatcaccccg      300
tcatacgccc gctcctga                                                     318
```

<210> SEQ ID NO 19
<211> LENGTH: 106
<212> TYPE: PRT
<213> ORGANISM: Rhodococcus erythropolis HL PM-1

<400> SEQUENCE: 19

Met Ile His Glu Leu Arg Glu Tyr Leu Ala Leu Pro Gly Arg Ala Glu
1               5                   10                  15

Asp Leu His Arg Arg Phe Ala Asp Asp Thr Leu Ala Leu Phe Ala Glu
            20                  25                  30

Phe Gly Leu Gln Val Glu Gly Phe Trp His Glu Ala Gly Asn Arg Ala
        35                  40                  45

Arg Ile Val Tyr Leu Leu Ala Phe Pro Asp Phe Glu Ala Ala Asp Ala
    50                  55                  60

His Trp Ala Arg Phe Gln Ala Asp Pro Arg Trp Cys Ala Leu Lys Ala
65                  70                  75                  80

Arg Thr Glu Ser Asp Gly Pro Leu Ile Ser Glu Ile Arg Ser Thr Phe
                85                  90                  95

Leu Ile Thr Pro Ser Tyr Ala Arg Ser Glx
            100                 105

<210> SEQ ID NO 20
<211> LENGTH: 1050
<212> TYPE: DNA
<213> ORGANISM: Rhodococcus erythropolis HL PM-1

<400> SEQUENCE: 20
atgatcaaag gcatccagct ccatggttgg gctgacgggc cgcagatggt cgaagtggcc      60
gagatcgccg ctgggagttt cgaaaccgtc tggctcagtg accaactcca gtcccgaggc     120
gtcgccgttc tcctcggcgc aatcgctgcg cgcaccggtg tcggagtcgg cactgcagtg     180
acctttccct tcgggcggaa ccccctcgag atggcatcca gcatggccac cctggcggag     240
ttcatgcccg aaggacgtcg ggtcaccatg gaatcggca ccgagg tgg gctggtgagt     300 gcgctcatgc cgctgcagaa cccgatcgac cgcgtggccg agttcatcgc gatgtgccgg     360
cttctctggc agggcgaagc gatccgaatg ggtgactacc acagatctg taccgccctc     420 ggcttgcgtg aggatgctcg ggcgtcgttc tcctggacga gcaagcccga cgtgcgcgtc     480
gtcgtcgccg cgccggacc gaaagtgctg agatgccg cgaactcgc agacggcgtc     540 atctgcgcca gcaatttccc ggcccacagc ctcgcggcct tccgtagcgg ccagttcgac     600
gcggtgagca acctcgatgc gctcgaccgg ggccgaaagc gcagtcggcg ggggagttc     660 acccggatct acggcgtgaa cctgtccgtg tctgccgacc gggagagtgc ctgcgcggcc     720
gcgcggcgac aggcgacact cattgtgagc caacagcctc cagagaatct gcaccgggtc     780
ggctttgagc cctccgacta cgccgccacc cgagcggcgc tcaaagccgg agacggcgta     840
gacgcagccg ccgacctcct cccacaggaa gtcgcggacc aactcgtggt ctcgggcacg     900
cccggcgact gcatcgaggc gctggccgag ctgctcgggt acgcggagga tgccggattc     960
accgaggcct acatcggtgc cccggtcggc ccggacccac gcgaggcggt cgagctcctc    1020
acgtcccagg tcctgccgga gctcgcatga                                    1050

<210> SEQ ID NO 21
<211> LENGTH: 350
<212> TYPE: PRT
<213> ORGANISM: Rhodococcus erythropolis HL PM-1

<400> SEQUENCE: 21

```
Met Ile Lys Gly Ile Gln Leu His Gly Trp Ala Asp Gly Pro Gln Met
  1               5                  10                  15
Val Glu Val Ala Glu Ile Ala Ala Gly Ser Phe Glu Thr Val Trp Leu
                 20                  25                  30
Ser Asp Gln Leu Gln Ser Arg Gly Val Ala Val Leu Leu Gly Ala Ile
             35                  40                  45
Ala Ala Arg Thr Gly Val Gly Val Gly Thr Ala Val Thr Phe Pro Phe
         50                  55                  60
Gly Arg Asn Pro Leu Glu Met ala Ser Ser Met ala Thr Leu Ala Glu
 65                  70                  75                  80
Phe Met Pro Glu Gly Arg Arg Val Thr Met Gly Ile Gly Thr Gly Gly
                 85                  90                  95
Gly Leu Val Ser Ala Leu Met Pro Leu Gln Asn Pro Ile Asp Arg Val
            100                 105                 110
Ala Glu Phe Ile Ala Met Cys Arg Leu Leu Trp Gln Gly Glu Ala Ile
        115                 120                 125
Arg Met Gly Asp Tyr Pro Gln Ile Cys Thr Ala Leu Gly Leu Arg Glu
    130                 135                 140
Asp Ala Arg Ala Ser Phe Ser Trp Thr Ser Lys Pro Asp Val Arg Val
145                 150                 155                 160
Val Val Ala Gly Ala Gly Pro Lys Val Leu Glu Met ala Gly Glu Leu
                165                 170                 175
Ala Asp Gly Val Ile Cys Ala Ser Asn Phe Pro Ala His Ser Leu Ala
            180                 185                 190
Ala Phe Arg Ser Gly Gln Phe Asp Ala Val Ser Asn Leu Asp Ala Leu
        195                 200                 205
Asp Arg Gly Arg Lys Arg Ser Arg Arg Gly Glu Phe Thr Arg Ile Tyr
    210                 215                 220
Gly Val Asn Leu Ser Val Ser Ala Asp Arg Glu Ser Ala Cys Ala Ala
225                 230                 235                 240
Ala Arg Arg Gln Ala Thr Leu Ile Val Ser Gln Gln Pro Pro Glu Asn
                245                 250                 255
Leu His Arg Val Gly Phe Glu Pro Ser Asp Tyr Ala Ala Thr Arg Ala
            260                 265                 270
Ala Leu Lys Ala Gly Asp Gly Val Asp Ala Ala Ala Asp Leu Leu Pro
        275                 280                 285
Gln Glu Val Ala Asp Gln Leu Val Val Ser Gly Thr Pro Gly Asp Cys
    290                 295                 300
Ile Glu Ala Leu Ala Glu Leu Leu Gly Tyr Ala Glu Asp Ala Gly Phe
305                 310                 315                 320
Thr Glu Ala Tyr Ile Gly Ala Pro Val Gly Pro Asp Pro Arg Glu Ala
                325                 330                 335
Val Glu Leu Leu Thr Ser Gln Val Leu Pro Glu Leu Ala Glx
            340                 345                 350
```

<210> SEQ ID NO 22
<211> LENGTH: 711
<212> TYPE: DNA
<213> ORGANISM: Rhodococcus erythropolis HL PM-1

<400> SEQUENCE: 22

```
atgagcgccg gcacgcaggc aacccgggac ctgtgcccgg ccgaacacca cgacggtctg    60
```

-continued

```
gtcgtcctga cgctcaatcg tcccgaggcg cgcaacgccc tcgacgtacc cctgctcgag      120
gcgttcgccg ctcggcttgc cgagggaaaa cgcgcgggcg ccggcgtcgt cctcgtgcgc      180
gcggaagggc cggcgttctg cgcaggagcc gatgtgcgtt ccgacgacgg cacggcgacc      240
ggccgaccgg gcctccggcg ccgtctcatc gaggagagcc tcgacctgct gggcgactac      300 ccggcggcg tggtcgcggt gcagggcgcc gcgatcggcg ccgggtgggc aatagccgcg      360
gcagcggaca tcacgctggc ctcgcctacc gcttcgttcc gatttcccga gctcccactc      420
ggattcccgc ccctgacag cacggtgcga atactcgaag ccgccgtcgg cccggcgcgg      480
gcgctgcggc tcctggccct gaacgagcgc ttcgtcgccg acgacctggc caggctcggt      540
ctggtggacg tcgttcccga ggattcgctc gacgtgacgg cgcgcgagac ggccgcccga      600
ctcgcggttc ttcccctcga gttgctgcgc gatctcaaaa caggcctctc cgccgggaag      660
cggcccccct ccatcgaccg accagcctcg aaaggcagtc atgagcacta g               711
```

<210> SEQ ID NO 23
<211> LENGTH: 237
<212> TYPE: PRT
<213> ORGANISM: Rhodococcus erythropolis HL PM-1

<400> SEQUENCE: 23

```
Met Ser Ala Gly Thr Gln Ala Thr Arg Asp Leu Cys Pro Ala Glu His
 1               5                  10                  15

His Asp Gly Leu Val Val Leu Thr Leu Asn Arg Pro Glu Ala Arg Asn
            20                  25                  30

Ala Leu Asp Val Pro Leu Leu Glu Ala Phe Ala Ala Arg Leu Ala Glu
        35                  40                  45

Gly Lys Arg Ala Gly Ala Val Val Leu Val Arg Ala Glu Gly Pro
    50                  55                  60

Ala Phe Cys Ala Gly Ala Asp Val Arg Ser Asp Asp Gly Thr Ala Thr
65                  70                  75                  80

Gly Arg Pro Gly Leu Arg Arg Leu Ile Glu Glu Ser Leu Asp Leu
                85                  90                  95

Leu Gly Asp Tyr Pro Ala Ala Val Ala Val Gln Gly Ala Ala Ile
            100                 105                 110

Gly Ala Gly Trp Ala Ile Ala Ala Ala Asp Ile Thr Leu Ala Ser
        115                 120                 125

Pro Thr Ala Ser Phe Arg Phe Pro Glu Leu Pro Leu Gly Phe Pro Pro
    130                 135                 140

Pro Asp Ser Thr Val Arg Ile Leu Glu Ala Ala Val Gly Pro Ala Arg
145                 150                 155                 160

Ala Leu Arg Leu Leu Ala Leu Asn Glu Arg Phe Val Ala Asp Asp Leu
                165                 170                 175

Ala Arg Leu Gly Leu Val Asp Val Val Pro Glu Asp Ser Leu Asp Val
            180                 185                 190

Thr Ala Arg Glu Thr Ala Ala Arg Leu Ala Val Leu Pro Leu Glu Leu
        195                 200                 205

Leu Arg Asp Leu Lys Thr Gly Leu Ser Ala Gly Lys Arg Pro Pro Ser
    210                 215                 220

Ile Asp Arg Pro Ala Ser Lys Gly Ser His Glu His Glx
225                 230                 235
```

<210> SEQ ID NO 24
<211> LENGTH: 1098
<212> TYPE: DNA

-continued

<213> ORGANISM: Rhodococcus erythropolis HL PM-1

<400> SEQUENCE: 24

```
atgagcacta gcattcacat tcagaccgac gagcaggcgc acctccgcac cactgcccgg     60
gcattcctgg ccagacacgc tcccgcgctc gacgtgcgca tctgggacga ggcggggaaa    120
taccccgagc acctgttccg cgagatcgcc cgcctcgggt ggtacgacgt ggtggccgga    180
gacgaggtcg tcgacggtac ggccggcctg ctgatcacgc tctgcgaaga gatcggccgg    240
gcgagttcgg aacctcgtgg ccttgttcaac ctgaacctca gtgggctgcg cgacatccac    300
cgctggggca cgcccgaaca gcaggagacg tacggtgcac cggtgctggc cggcgaggcg    360
cgcctgtcga tcgcggtgag cgaacccgac gtgggctcgg acgccgcgag cgtggccacg    420
cgcgccgaga aggtcgggga ctcgtggatc ctcaacggcc agaagaccta ctgcgagggc    480
gcgggactaa ccggcgcagt aatggaactc gtcgcccgag tgggagggg tggtcgcaag    540
cgcgaccaac tcgccatatt tctggtgccg gtcgatcatc cggggtcga ggtccgccgc    600
atgcccgcgc tcggccggaa catcagcgga atctacgagg tcttcctgcg ggacgttgcg    660
cttccggcga cggcggtgct gggtgagccc ggtgaaggat ggcagatcct caaggaacgt    720
ctggtgctcg agcggatcat gatcagttcc ggcttcctcg gcagcgtcgc cgcggtactc    780
gacctgacgg tccactacgc caacgagcgc gagcagttcg gcaaggcact ctcgagctat    840
cagggcgtga ccttgcccct cgccgagatg ttcgtcaggc tcgacgcggc ccagtgcgcg    900
gtacgccgtt cggccgacct cttcgacgcg gtctgccgt gcgaggtgga gagcacgatg    960
gcgaagttcc tctccggcca gctctacgcg gaggcctctg ctctggcgat gcagattcag    1020
ggcgcctacg gctatgtgcg cgaccatgcc ttgccgatgc accactccga cgggatcccc    1080
gggtaccgag ctcgaatt                                                  1098
```

<210> SEQ ID NO 25
<211> LENGTH: 366
<212> TYPE: PRT
<213> ORGANISM: Rhodococcus erythropolis HL PM-1

<400> SEQUENCE: 25

```
Met Ser Thr Ser Ile His Ile Gln Thr Asp Glu Gln Ala His Leu Arg
  1               5                  10                  15

Thr Thr Ala Arg Ala Phe Leu Ala Arg His Ala Pro Ala Leu Asp Val
             20                  25                  30

Arg Ile Trp Asp Glu Ala Gly Lys Tyr Pro Glu His Leu Phe Arg Glu
         35                  40                  45

Ile Ala Arg Leu Gly Trp Tyr Asp Val Val Ala Gly Asp Glu Val Val
     50                  55                  60

Asp Gly Thr Ala Gly Leu Leu Ile Thr Leu Cys Glu Glu Ile Gly Arg
 65                  70                  75                  80

Ala Ser Ser Asp Leu Val Ala Leu Phe Asn Leu Asn Leu Ser Gly Leu
                 85                  90                  95

Arg Asp Ile His Arg Trp Gly Thr Pro Glu Gln Gln Glu Thr Tyr Gly
            100                 105                 110

Ala Pro Val Leu Ala Gly Glu Ala Arg Leu Ser Ile Ala Val Ser Glu
        115                 120                 125

Pro Asp Val Gly Ser Asp Ala Ala Ser Val Ala Thr Arg Ala Glu Lys
    130                 135                 140

Val Gly Asp Ser Trp Ile Leu Asn Gly Gln Lys Thr Tyr Cys Glu Gly
145                 150                 155                 160
```

```
Ala Gly Leu Thr Gly Ala Val Met Glu Leu Val Ala Arg Val Gly Gly
                165                 170                 175
Gly Gly Arg Lys Arg Asp Gln Leu Ala Ile Phe Leu Val Pro Val Asp
            180                 185                 190
His Pro Gly Val Glu Val Arg Arg Met Pro Ala Leu Gly Arg Asn Ile
            195                 200                 205
Ser Gly Ile Tyr Glu Val Phe Leu Arg Asp Val Ala Leu Pro Ala Thr
            210                 215                 220
Ala Val Leu Gly Glu Pro Gly Glu Gly Trp Gln Ile Leu Lys Glu Arg
225                 230                 235                 240
Leu Val Leu Glu Arg Ile Met Ile Ser Ser Gly Phe Leu Gly Ser Val
                245                 250                 255
Ala Ala Val Leu Asp Leu Thr Val His Tyr Ala Asn Glu Arg Glu Gln
                260                 265                 270
Phe Gly Lys Ala Leu Ser Ser Tyr Gln Gly Val Thr Leu Pro Leu Ala
                275                 280                 285
Glu Met Phe Val Arg Leu Asp Ala Ala Gln Cys Ala Val Arg Arg Ser
            290                 295                 300
Ala Asp Leu Phe Asp Ala Gly Leu Pro Cys Glu Val Glu Ser Thr Met
305                 310                 315                 320
Ala Lys Phe Leu Ser Gly Gln Leu Tyr Ala Glu Ala Ser Ala Leu Ala
                325                 330                 335
Met Gln Ile Gln Gly Ala Tyr Gly Tyr Val Arg Asp His Ala Leu Pro
                340                 345                 350
Met His His Ser Asp Gly Ile Pro Gly Tyr Arg Ala Arg Ile
                355                 360                 365

<210> SEQ ID NO 26
<211> LENGTH: 17
<212> TYPE: DNA
<213> ORGANISM: Artificial Sequence
<220> FEATURE:
<221> NAME/KEY: unsure
<222> LOCATION: ()..()
<223> OTHER INFORMATION: V = A, G or C  (all combinations of these three
      bases at the last five positions)
<223> OTHER INFORMATION: Description of Artificial Sequence:  primer
<223> OTHER INFORMATION: primer

<400> SEQUENCE: 26
cggagcagat cgvvvvv                                                    17

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:  primer
<223> OTHER INFORMATION: primer

<400> SEQUENCE: 27
agtccacgga gcatatcg                                                   18

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence:  primer
<223> OTHER INFORMATION: common region of the 240 primers used in the
      instant invention
```

-continued

<400> SEQUENCE: 28
cggagcagat cg                                                                 12

GENES ENCODING PICRIC ACID DEGRADATION

This is a Divisional application claiming priority to U.S. Ser. No. 09/651,941, filed Aug. 31, 2000, issued as U.S. Pat. No. 6,355,470 which claims the benefit of Provisional Application U.S. Ser. No. 60/152,545, filed Sep. 3, 1999.

FIELD OF THE INVENTION

The invention relates to the field of molecular biology and microbiology. More specifically, a 12 kb gene cluster has been isolated from *Rhodococcus erythropolis* HL PM-1 containing several open reading frames implicated in the degradation of picric acid.

BACKGROUND OF THE INVENTION

Picric acid (2,4,6-trinitrophenol) is a compound used in a variety of industrial applications including the manufacture of explosives, aniline, color fast dyes, pharmaceuticals and in steel etching. Picric acid and ammonium picrate were first obtained as fast dyes for silk and wool. However, the unstable nature of picric acid was soon exploited for use as an explosive and explosive boosters where it is the primary component of blasting caps which are used for the detonation of 2,4,6-trinitrotoluene (TNT). Because of its explosive nature, disposal of waste picric acid poses unique hazard not generally associated with other environmental toxicants.

Mounting public concern and increasing government regulations have provided the impetus for a safe, effective means to remediate picric acid contaminated environments. Past methods of disposing of munitions and other wastes containing picric acid have included dumping at specified land-fill areas, isolation in suitable, reinforced containers, land based deep-welling, dumping in deep water at sea and incineration. All of these methods carry some potential for harm to the environment. For example, incineration creates a problem of air pollution and disposal on land risks the possibility that toxic substances will elute or leach into locations where they may threaten aquatic life forms, animals or humans. A more desirable disposal method might incorporate a chemical or enzymatic degradative process.

The metabolic reduction of organic nitrogen groups has been known for some time. Westfall (*J. Pharmacol. Exp. Therap.* 78:386 (1943)) reported that liver, kidney and heart tissue are active in the reduction of trinitrotoluene, however, was not able to identify the specific enzyme system responsible. Westerfield et al. (*J. Biol. Chem.* 227:379 (1957)) further disclosed that purified xanthine oxidase is capable of reducing organic nitrogen groups and demonstrated that the molybdenum (Mo) co-factor was essential in the degradative process.

Microbial degradation of organic nitrogen compounds has been limited to a handful of organisms. Erickson (*J. Bacteriol.* 41:277 (1941)) reported that certain strains of Micromonospora were able to utilize picric acid and trinitroresorcinol as a carbon source and Moore (*J. Gen. Microbiol.*, 3:143 (1949)) described two unspecified Proactinomnycetes as being capable of using nitrobenzene as a simultaneous source of carbon and nitrogen. Gundersden et al. (*Acta. Agric. Scand.* 6:100 (1956)) described the metabolism of picric acid by *Corynebacterium simplex* which was isolated from soil as a 4,6-dinitro-2-methylphenol-degrading organism. Degradation was determined by measuring the amount of nitrate produced when the organism was contacted with an organic nitrogen compound. The extent of degradation and the identification of specific degradation products were not reported. Later, Wyman et al. (*Appl. Environ. Microbiol.* 37 (2):222 (1979)) found that a strain of *Pseudomonas aeruginosa* reduced picric acid to 2-amino-4,6-dinitrophenol (picramic acid) under anaerobic conditions. Wyman further determined that degradation products from both picric and picramic acid produced by this strain demonstrated mutagenicity as assayed by the standard AMES test.

Another Pseudomonas sp., *Pseudomonas putida*, has been shown to be able to use picric acid as a carbon source and achieve some bio-conversion of the compound to 1,3,5-trinitrobenzene, 2,4,6-trinitroaldehyde, and 3,5-dinitrophenol (Kearney et al., *Chemosphere*, 12 (11–12): 1583 (1983)).

Recently, *Rhodococcus erythropolis* has been identified a picric acid degrading bacteria. Lenke et al. (*Appl. Environ. Microbiol.* 58 (9):2933 (1992)) teach that *Rhodococcus erythropolis*, under aerobic conditions, can incompletely utilize picric acid as a nitrogen source producing nitrite and 2,4,6-trinitrocyclohexanone, which cannot be degraded further. More recently a consortium of bacteria comprising members of the genera Arthrobacter, Avrobacterium and Pseudomonas has been described that has the ability to completely degrade picric acid (U.S. Pat. No. 5,543,324). Similarly, U.S. Pat. No. 5,478,743 teaches Arthrobacter isolates having the ability to mineralize picric acid and other tri-nitrophenol compounds. In work growing out of these discoveries Ebert et al. (*J. Bacteriol.* 181 (9):2669–2674 (1999)) describe some of the possible intermediates in the picric acid bio-degradation pathway and teach the N-terminal sequence of an NADPH-dependent F420 reductase. No nucleotide sequence is disclosed and no description of other elements of the pathway are provided.

Although several wild type organisms having some ability to degrade picric acid and other nitroaromatics, have been described, to date, no genes have been identified or isolated from these or other organisms that might comprise a bio-degradative pathway for this persistent pollutant. The ability to manipulate the genes involved in the picric acid degradation pathway will greatly advance the art of picric acid remediation. If such genes are known, they may be transformed into suitable hosts and overexpressed in a manner so as to optimize the degradative process.

The problem to be solved therefore is to isolate genes involved in picric acid degradation for their eventual use in creating transformants with enhanced ability to degrade picric acid. Applicants have solved the stated problem by isolating a 12 kb DNA fragment containing ten open reading frames (ORF) which have distinct homology to genes expected to play significant role in the picric acid degradative pathway.

SUMMARY OF THE INVENTION

The present invention provides isolated nucleic acid fragments encoding enzymes of the picric acid degradation pathway corresponding to ORF's 3, 5, 6, 8, 9, 10 and 11 of the present 12 kb gene cluster where the isolated nucleic acid fragments are independently selected from the group consisting of (a) isolated nucleic acid fragment encoding all or a substantial portion of the amino acid sequence as set forth in SEQ ID NO:7, SEQ ID NO:11, SEQ ID NO:15, SEQ ID NO:17, SEQ ID NO:21, SEQ ID NO:23 and SEQ ID NO:25; (b) isolated nucleic acid fragments that are substantially similar to isolated nucleic acid fragments encoding all or a substantial portion of the amino acid sequences as set forth in SEQ ID NO:7, SEQ ID NO:11, SEQ ID NO:15, SEQ ID NO:17, SEQ ID NO:21, SEQ ID NO:23 and SEQ ID NO:25; (c) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS and; (d) and isolated nucleic acid fragments that are complementary to (a), (b) or (c).

The invention further provides the nucleic acid fragment embodying the 12 kb gene cluster comprising ORF's 1–12 of the instant invention, useful for the degradation of picric acid.

The invention also provides chimeric genes comprised of the instant nucleic acid fragments and suitable regulatory sequences as well as the polypeptides encoded by said sequences.

The invention further provides methods for obtaining all or a portion of the instant sequences by either primer directed amplification protocols or by hybridization techniques using primers or probes derived from the instant sequences.

Additionally the invention provides recombinant organisms transformed with the chimeric genes of the instant invention and methods of the degrading picric acid and dinitrophenol using said recombinant organisms.

The invention further provides a method for the conversion of picric acid to dinitrophenol comprising: contacting a transformed host cell under suitable growth conditions with an effective amount of picric acid whereby dinitrophenol is produced, said transformed host cell comprising a nucleic acid fragment encoding SEQ ID NO:21 under the control of suitable regulatory sequences.

In another embodiment the invention provides a mutated bacterial gene encoding an F420/NADPH oxidoreductase or an F420-dependent picric/2,4-DNP reductase, having an altered F420 dependent reductase activity produced by a method comprising the steps of (i) digesting a mixture of nucleotide sequences with restriction endonucleases wherein said mixture comprises:

a) a bacterial gene encoding a F420/NADPH oxidoreductase or an F420-dependent picric/2,4-DNP reductase;

b) a first population of nucleotide fragments which will hybridize to said wildtype bacterial sequence;

c) a second population of nucleotide fragments which will not hybridize to said wildtype bacterial sequence;
wherein a mixture of restriction fragments are produced; (ii) denaturing said mixture of restriction fragments; (iii) incubating the denatured said mixture of restriction fragments of step (ii) with a polymerase; and (iv) repeating steps (ii) and (iii) wherein a mutated bacterial gene is produced encoding a protein having an altered F420 dependent reductase activity.

BRIEF DESCRIPTION OF THE DRAWINGS AND SEQUENCE DESCRIPTIONS

Figure 8A:
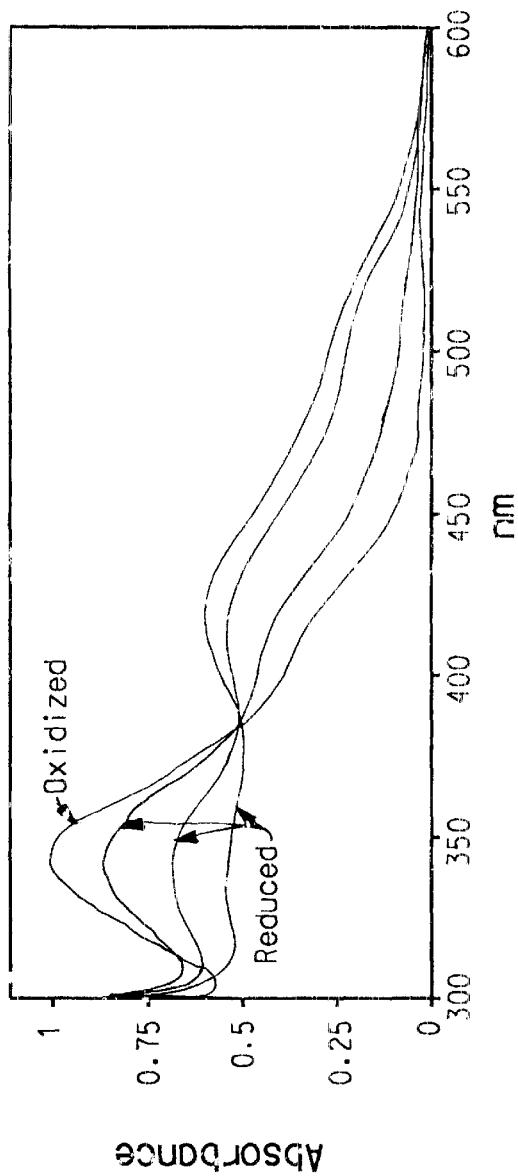

FIG. 8A presents a diagram showing the reduction of picric acid by E. coli cell extracts expressing the picric acid/DNP F420-dependent dehydrogenase (ORF9).

Figure 8B:
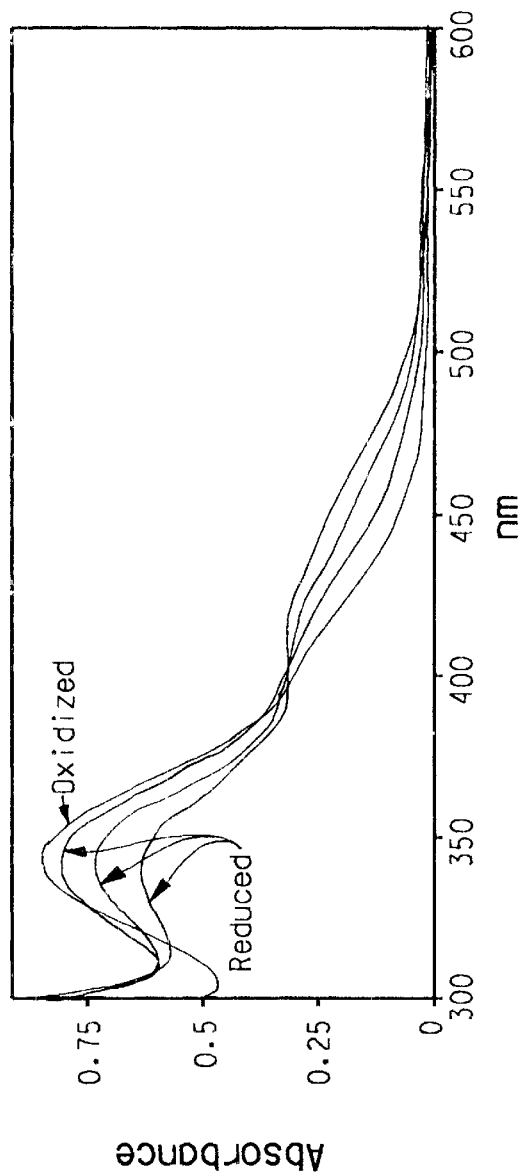

FIG. 8B presents a diagram showing the reduction of dinitrophenol by E. coli cell extracts expression the picric acid/DNP F420-dependent dehydrogenase (ORF9).

Figure 9:
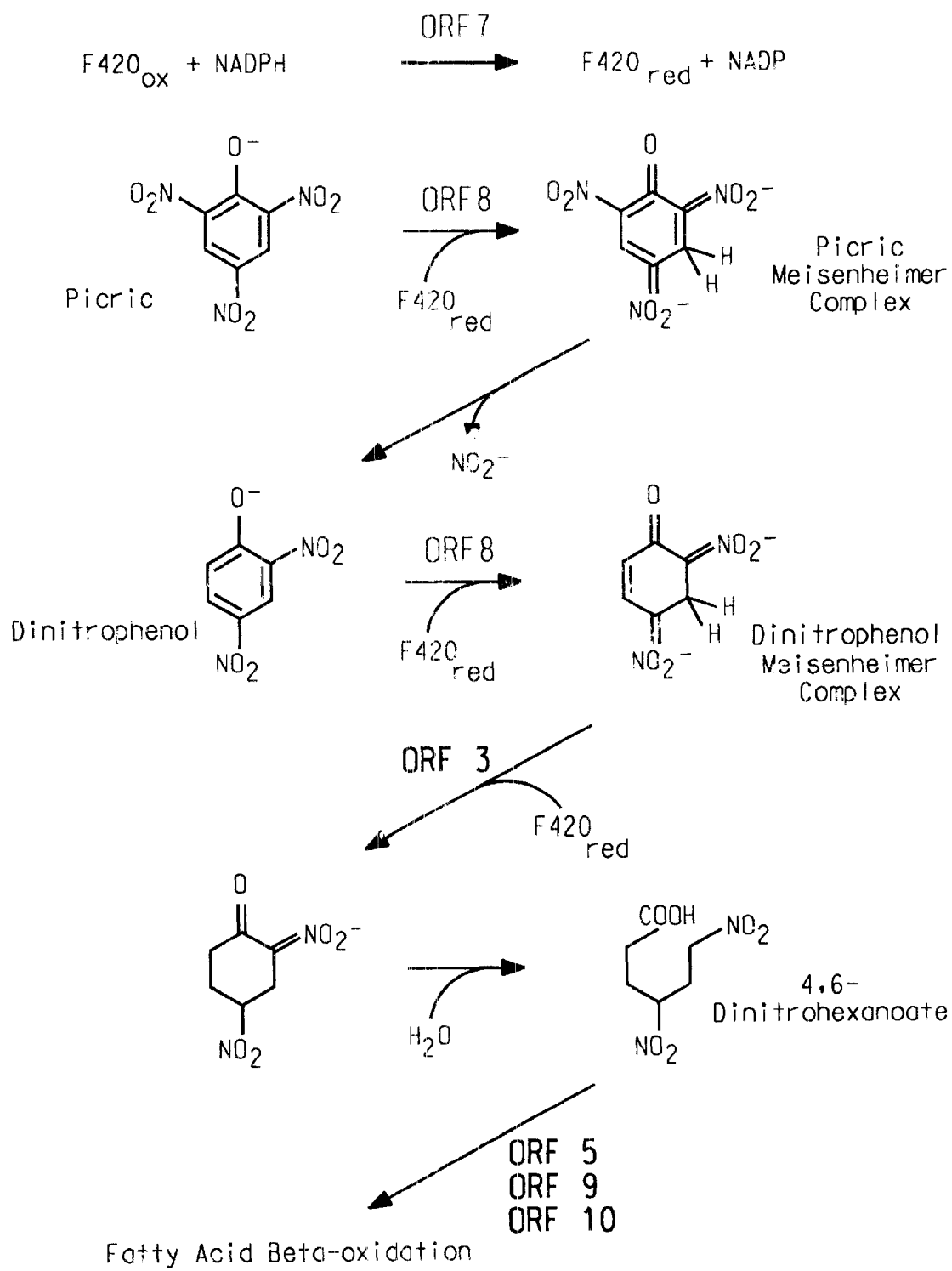

FIG. 9 is a diagram showing a proposed pathway for the degradation of picric acid and dinitrophenol and an assignment of biochemical functions for the enzymes encoded by the ORFs of the picric degradation gene cluster.

The invention can be more fully understood from the following detailed description and the accompanying sequence descriptions which form a part of this application.

Applicant(s) have provided 24 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the 12 kb picric acid degradation gene cluster from identified from *Rhodococcus erythropolis* HL PM-1 by high density sampling mRNA differential display in Example 1.

SEQ ID NO:2 is the partial nucleotide sequence of ORF1 of the picric acid degradation gene cluster from *Rhodococcus erythropolis* HL PM-1 encoding for a transcription factor.

SEQ ID NO:3 is the deduced amino acid sequence of ORF1 encoded by SEQ ID NO:2.

SEQ ID NO:4 is the nucleotide sequence of ORF2 of the picric acid degradation gene cluster from *Rhodococcus erythropolis* HL PM-1 encoding a dehydratase.

SEQ ID NO:5 is the deduced amino acid sequence of ORF2 encoded by SEQ ID NO:4.

SEQ ID NO:6 is the nucleotide sequence of ORF3 of the picric acid degradation gene cluster from *Rhodococcus erythropolis* HL PM-1 encoding an F420-dependent dehydrogenase.

SEQ ID NO:7 is the deduced amino acid sequence of ORF3 encoded by SEQ ID NO:6.

SEQ ID NO:8 is the nucleotide sequence of ORF4 of the picric acid degradation gene cluster from *Rhodococcus erythropolis* HL PM-1 encoding an aldehyde dehydrogenase.

SEQ ID NO:9 is the deduced amino acid sequence of ORF4 encoded by SEQ ID NO:8.

SEQ ID NO:10 is the nucleotide sequence of ORF5 of the picric acid degradation gene cluster from *Rhodococcus erythropolis* HL PM-1 encoding an acyl-CoA synthase.

SEQ ID NO:11 is the deduced amino acid sequence of ORF5 encoded by SEQ ID NO:10.

SEQ ID NO:12 is the nucleotide sequence of ORF6 of the picric acid degradation gene cluster from *Rhodococcus erythropolis* HL PM-1 encoding an glyoxalase.

SEQ ID NO:13 is the deduced amino acid sequence of ORF6 encoded by SEQ ID NO:12.

SEQ ID NO:14 is the nucleotide sequence of ORF7 of the picric acid degradation gene cluster from *Rhodococcus erythropolis* HL PM-1 encoding a Transcription regulator.

SEQ ID NO:15 is the deduced amino acid sequence of ORF7 encoded by SEQ ID NO:14.

SEQ ID NO:16 is the nucleotide sequence of ORF8 of the picric acid degradation gene cluster from *Rhodococcus erythropolis* HL PM-1 encoding an F420/NADPH oxidoreductase.

SEQ ID NO:17 is the deduced amino acid sequence of ORF8 encoded by SEQ ID NO:16.

SEQ ID NO:18 is the nucleotide sequence of ORF8.1 of the picric acid degradation gene cluster from *Rhodococcus erythropolis* HL PM-1 encoding a protein of unknown function.

SEQ ID NO:19 is the deduced amino acid sequence of ORF8 encoded by SEQ ID NO:18.

SEQ ID NO:20 is the nucleotide sequence of ORF9 of the picric acid degradation gene cluster from *Rhodococcus erythropolis* HL PM-1 encoding an F420-dependent picric/DNP dehydrogenase.

SEQ ID NO:21 is the deduced amino acid sequence of ORF9 encoded by SEQ ID NO:20.

SEQ ID NO:22 is the nucleotide sequence of ORF10 of the picric acid degradation gene cluster from *Rhodococcus erythropolis* HL PM-1 encoding an enoyl-CoA dehydratase.

SEQ ID NO:23 is the deduced amino acid sequence of ORF10 encoded by SEQ ID NO:22.

SEQ ID NO:24 is the nucleotide sequence of ORF11 of the picric acid degradation gene cluster from *Rhodococcus erythropolis* HL PM- 1 encoding an acyl-CoA dehydrogenase. This sequence is a partial sequence covering the first 1074 nucleotides of the gene.

SEQ ID NO:25 is the deduced amino acid sequence of ORF11 encoded by SEQ ID NO:24. This sequence is a partial sequence covering the first 358 amino acids of the protein.

SEQ ID NO:26 is the sequence of the arbitrary primer used in this study.

SEQ ID NO:27 is the sequence of the universal primer used for the reamplification of the differentially amplified bands SEQ ID NO:28 is the sequence of the common region of the 240 primers used in this study.

DETAILED DESCRIPTION OF THE INVENTION

The present invention provides a 12 kb gene cluster isolated from *Rhodococcus erythropolis* containing several open reading frames implicated in the degradation of picric acid. The genes and their expression products are useful for the creation of recombinant organisms that have the ability to degrade picric acid, and for the identification of new species of bacteria having the ability to degrade picric acid. Full length sequence for 8 of the 10 ORF's have been obtained and identified by comparison to public databases containing nucleotide and protein sequences using the BLAST algorithms well known to those skilled in the art.

In this disclosure, a number of terms and abbreviations are used. The following definitions are provided.

"Open reading frame" is abbreviated ORF.

"Polymerase chain reaction" is abbreviated PCR.

"Differential Display" is abbreviated DD.

"Random amplification of polymorphic DNA" is abbreviated RAPD.

"Dinitrophenol" is abbreviated DNP.

"RAPD patterns" refer to patterns of arbitrarily amplified DNA fragments separated by electrophoresis "RT-PCR" is the abbreviation for reverse transcriptase polymerase chain reaction.

"Universal reamplification primer" refers to a primer including at its 3' end the nucleotide sequence common to 5' end of all arbitrary primers the present invention.

"Specific primer refers" to the arbitrary primer originally used in an RT-PCR reaction to generate a differentially amplified RAPD DNA fragment and which is then subsequently used for the reamplification of same RAPD bands eluted from the polyacrylamide gel.

"Universal primer refers" to a primer that includes at its 3' end a sequence common to the 5' end of all arbitrary primers of the collection and which can thus be used to reamplify by PCR any DNA fragment originally amplified by any arbitrary primer of the primer collection.

The term "differential display" will be abbreviated "(DD)" and is a technique in which mRNA species expressed by a cell population are reverse transcribed and then amplified by many separate polymerase chain reactions (PCR). PCR primers and conditions are chosen so that any given reaction yields a limited number of amplified cDNA fragments, permitting their visualization as discrete bands following gel electrophoresis or other detection techniques. This procedure allows identification of genes that are differentially expressed in different cell populations.

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase. Wherein the primer contains a sequence complementary to a region in one strand of a target nucleic acid sequence and primes the synthesis of a complementary strand, and a second primer contains a sequence complementary to a region in a second strand of the target nucleic acid and primes the synthesis of complementary strand; wherein each primer is selected to hybridize to its complementary sequence, 5' to any detection probe that will anneal to the same strand.

A primer is called "arbitrary" in that it can be used to initiate the enzymatic copying of a nucleic acid by a reverse transcriptase or a DNA polymerase even when its nucleotide sequence does not complement exactly that of the nucleic acid to be copied. It is sufficient that only part of the sequence, in particular the five to eight nucleotides at the 3' end of the molecule, hybridize with the nucleic acid to be copied. For that reason no sequence information of the template nucleic acid need to be known to design or the primer. The sequence of the primer can be designed randomly or systematically as described in this invention. "Arbitrary primers" of the present invention are used in collections so that there are at least 32 primers in a collection. Each of the arbitrary primers comprise a "common region" and a "variable region". The term "common region" as applied to an arbitrary primer means that region of the primer sequence that is common to all the primers used in the collection. The term "variable region" as applied to an arbitrary primer refers to a 3' region of the primer sequence that is randomly generated. Each of the primers in a given collection is unique from another primer, where the difference between the primers is determined by the variable region.

As used herein "low stringency" in referring to a PCR reaction will mean that the annealing temperature of the reaction is from about 30° C. to about 40° C. where 37° C. is preferred.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "picric acid degrading gene" means any gene or open reading frame of the present invention that is implicated in the degradation of picric acid. As used herein "picric acid degrading gene" will specifically refer to any one of the ten open reading frames encoding the polypeptides identified by SEQ ID NO's:3, 5, 7, 9, 11, 13, 17, 21, 23, and 25

The term "picric acid degrading enzyme" means the gene product of any of ORF 3, ORF 5, ORF 6, ORF 8, ORF 9, ORF 10 and ORF 11 encoding SEQ ID NO:7, SEQ ID NO:11, SEQ ID NO:13, SEQ ID NO:17, and SEQ ID NO:21, SEQ ID NO:23 and SEQ ID NO:25, respectively.

The term "F420-Dependent NADP oxidoreductase refers to an enzyme involved in the reduction of the F420 cofactor in the presence of NADPH. In the context of the present invention this enzyme is encoded by ORF 8 (SEQ ID NO:16) and is resident on the 12 kb DNA gene cluster (SEQ ID NO:1).

The term "F420-dependent dehydrogenase" refers to an enzyme involved in the reduction of an organic molecule using reduced equivalents from reduced F420. Within the context of the present invention, F420-dependent dehydrogenase refers to two enzymes encoded by ORF 3 (SEQ ID NO:6) and ORF 9 (SEQ ID NO:20) and are resident on the 12 kb DNA gene cluster (SEQ ID NO:1).

The term "F420-dependent picric/dinitrophenol dehydrogenase" refers to the specific F420-dependent reductase capable of reducing picric acid and 2,4-dinitrophenol into their respective Meisenheimer complexes (FIG. 9). Within the context of the present invention this enzyme is encoded by ORF 9 (SEQ ID NO:20) and is resident on the 12 kb DNA gene cluster (SEQ ID NO:1).

The term "acyl-coenzyme A synthase" refers to an enzyme that forms a thioester bond between the carboxyl group of a fatty acid molecule and the thiol group of the cofactor coenzyme A, and is encoded by ORF 5 of the present invention.

The term "enoyl-CoA hydratase" refers to an enzyme that catalyzes the reversible hydratation of a double bond in the beta position of a fatty acid chain, and is encoded by ORF 10 of the present invention.

The term "acyl-CoA dehydrogenase" refers to an enzyme that catalyzes the oxidation of the carbon bond in the beta position of a fatty acid to form a double bond; and is encoded by ORF 11 of the present invention.

The term "gene cluster" will mean genes organized in a single expression unit or physically associated with each other.

The term "12 kb nucleic acid fragment" refers to the 12 kb gene cluster comprising ORFs 1–12 necessary for the degradation of picric acid.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F. et al., *J. Mol. Biol.* 215:403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. "Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant bacterial polypeptides as set forth in SEQ ID NO's:3, 5, 7, 9, 11, 13, 15, 17, 19, 21, 23, and 25. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a bacterial nucleotide sequence which can be measured by an assay method, where that activity is either greater than or less than the activity associated with the native or wild type bacterial sequence. "Enhanced biological activity" refers to an altered activity that is greater than that associated with the wild type sequence. "Diminished biological activity" is an altered activity that is less than that associated with the wild type sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a 12 kb gene cluster comprising ten open reading frames that encode enzyme activities implicated in the biodegradation of picric acid. The 12 kb gene cluster was isolated from *Rhodococcus erythropolis* HL PM-1 by a method employing differential display and amplification of induced RNA message by reverse transcriptase PCR. This is the first instance where a number of the genes involved in picric acid degradation have been identified and sequenced.

The evidence for the identity and function of the present genes is based on the homology comparisons with known sequences in public databases as well as the method and circumstances of their isolation. For example, it is well known that genes involved in degradation pathways in prokaryotes are generally clustered in operons that correspond to functional units. Typically these operons have a transcription factor in at the beginning of the cluster such as is seen in the present ORF 1. Additional transcription factors are often seen throughout the rest of the gene cluster, similar to the present ORF 7. Although the pathway for the degradation of picric acid and dinitrophenol is only partially known, it is clear that ORF's 8 and 9 play an important role. The involvement of two F420-dependent enzymes have been demonstrated biochemically in a Nocardia species. One enzyme is F420/NADPH oxidoreductase while the other is an F420-dependent dehydrogenase that catalyzes the reduction of picric acid and 2,4-dinitrophenol into their respective Meisenheimer complexes. The activities of both enzymes have been validated biochemically as being involved in the reduction of picric and dinitrophenol (Ebert et al., *J. Bacteriol.* 181 (9):2669–2674 (1999); Behrend and Heesche-Wagner, *Appl. Environ. Microbiol.* 65 (4):1372–1377 (1999)). Sequence similarities combined with expression experiments demonstrated that the enzyme encoded by ORF 8 is an a F420-dependent oxidoreductase responsible for the regeneration of the reduced F420 cofactor (F420/NADPH oxidoreductase) and that the enzyme product of ORF 9 catalyzes the reduction of 2,4-dinitrophenol (DNP) to the DNP-Meisenheimer complex and that of picric acid to the Picric-Meisenheimer complex (FIG. 9). It is contemplated that the enzyme encoded by ORF 3 (a second putative F420-dependent dehydrogenase) will be effective in the second reduction of the DNP-Meisenheimer complex on the conjugated double bond of the ring by another hydride transfer (FIG. 9). A subsequent spontaneous hydrolytic ring cleavage would yield 4,6-dinitrohexanoate which is the only other known intermediate in the degradation pathway (Ebert et al., *J. Bacteriol.* 181 (9):2669–2674 (1999)). This substituted fatty acid is most likely to be oxidized like other fatty acids by the beta-oxidation pathway. This typically involves the activation of the terminal carboxyl-group with coenzyme A by an acyl-coenzyme A synthase (ORF 5), the oxidation of the C-C bond in the beta position by an acyl-CoA dehydrogenase (ORF 11), the hydration of the double bond in the beta position by an enoyl-CoA hydratase (ORF 10).

Isolation of Gene Homologs

The nucleic acid fragments of the instant invention may be used to isolate cDNAs and genes encoding homologous proteins from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g polymerase chain reaction (PCR), Mullis et al., U.S. Pat. No. 4,683,202), ligase chain reaction (LCR), Tabor, S. et al., *Proc. Acad. Sci. U.S.A.* 82, 1074, (1985)) or strand displacement amplification (SDA, Walker et al., *Proc. Natl. Acad. Sci. U.S.A.* 89:392, (1992)).

For example, genes encoding similar proteins or polypeptides to those of the instant invention, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate fall length cDNA or genomic fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from five bases to tens of thousands of bases, and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Specifically, any one of the gene identification and isolation methods described above may be used in conjunction with the present picric acid degrading genes to identify other organisms capable of picric acid or dinitrophenol degradation. Additionally, the genes encoding the F420 dependent enzymes, ORF 8 and 9, above can be used in genetic experiments to detect and identify the genes involved in the biosynthesis of F420.

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. *Adv. Immunol.* 36:1 (1984); Maniatis).

Overexpression in Microorganisms

The genes and gene products of the instant sequences may be produced in heterologous host cells, particularly in the cells of microbial hosts, and can be used to create transformants capable of picric acid degradation on a commercial scale.

Preferred heterologous host cells for production of the instant proteins are microbial hosts. Specific suitable hosts include but are not limited to, organisms that produce factor F420 naturally such as Mycobacterium, Rhodococcus, Streptomyces, Nocardia, Arthrobacter, Methanobacterium, Methanococcus, Methanosarcina and Archaeoglobus. The simultaneous introduction in a host organism of the genes involved in the synthesis of the a complete or a part of the deazaflavin Factor F420 could allow the utilization of other microbial hosts such as Aspergillus, Saccharomyces, Pichia, Candida, Hansenula, Salmonella, Bacillus, Acinetobacter, Escherichia and Pseudomonas.

For example the genes encoding the F420/NADPH oxidoreductase (ORF 8) and the F420-dependent picric/2,4-DNP dehydrogenase (ORF 9) could be used in tandem to create screens for the identification of genes involved in the synthesis of factor F420. It is contemplated for example that a cell, not naturally able to synthesize F420 could be transformed with ORF 8 and ORF 9 of the present invention. This transformant could then be selectively transformed with specific DNA from F420 synthesizing organisms (including but not limited to Mycobacterium, Streptomyces, Nocardia, Arthrobacter, Methanobacterium, Methanococcus, Methanosarcina and Archaeoglobus), and the transformant would be monitored for the ability to convert the yellow picric acid or dinitrophenol into their respective orange Meisenheimer complexes. In this fashion, genes involved in the synthesis of factor F420 could be indentified.

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in *Escherichia coli*).

Termination control regions may also be derived from various genes native to the preferred hosts. Optionally, a termination site may be unnecessary, however, it is most preferred if included.

Protein Evolution

It is contemplated that the present nucleotide may be used to produce gene products having enhanced or altered activity. Various methods are known for mutating a native or wild type gene sequence to produce a gene product with altered or enhanced activity including but not limited to error prone PCR (Melnikov et al., *Nucleic Acids Res.* 27:4 1056–1062 (1999)); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction of a gene of interest into fragments of specific size in the presence of additional populations of DNA regions of both similarity to or difference to the gene of interest. This collection of fragments wit then denatured and then reannealed to create a mutate gene. The mutated gene is then screened for altered activity.

The instant bacterial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant bacteria sequences populations of fragments that are hybridizable to all or portions of the bacterial sequence may added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75°

C. Renaturation can be accelerated by the addition of polyethylene glycol ("PEG") or salt. The salt concentration is preferably from 0 mM to 200 mM. The annealed nucleic acid fragments are next incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered activity by standard cloning and expression protocol. (Maniatis supra).

DESCRIPTION OF THE PREFERRED EMBODIMENTS

Figure 5:
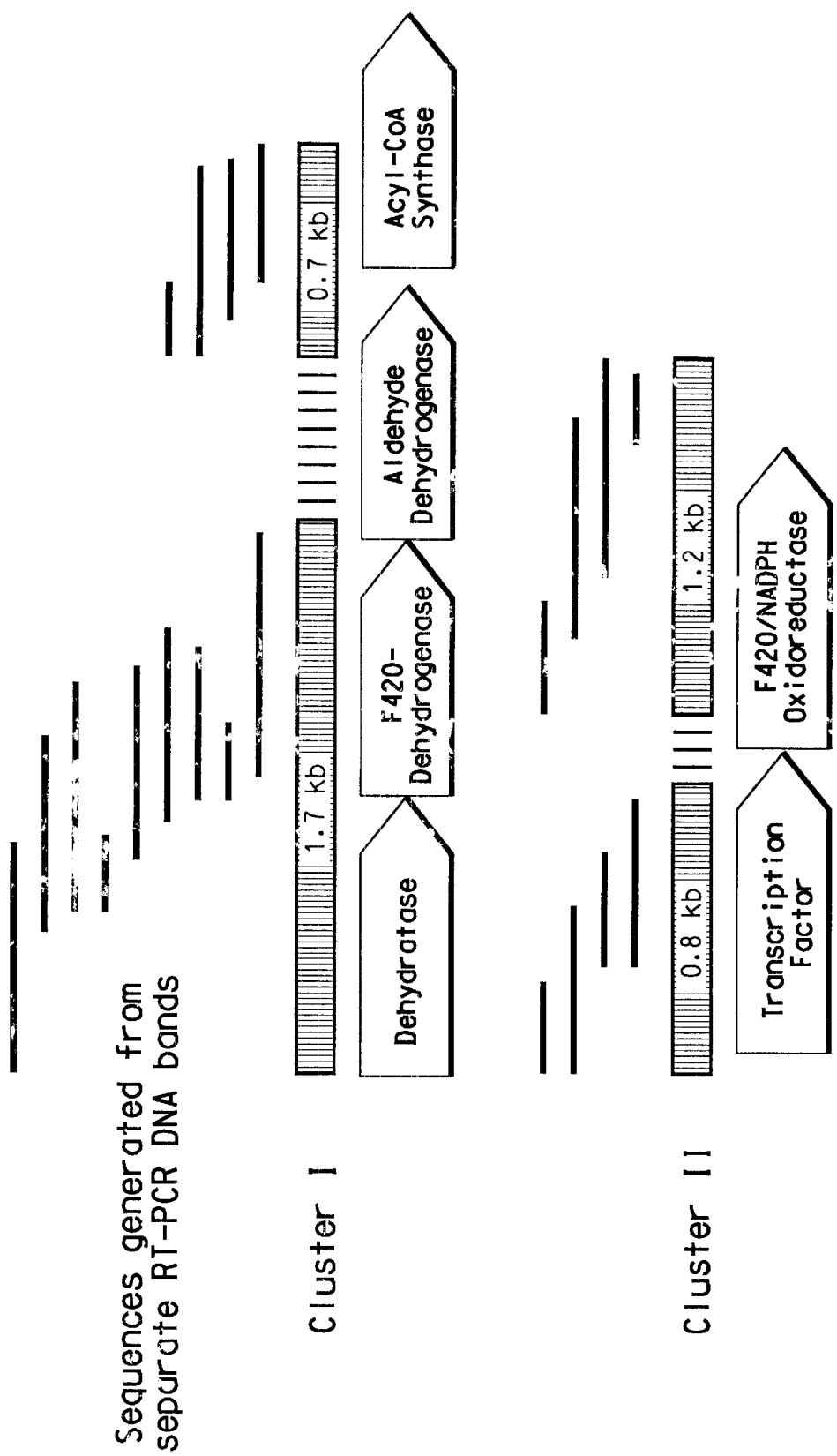
FIG. 5 is a diagram showing contig assembly from sequences of differentially expressed bands.
Figure 6:
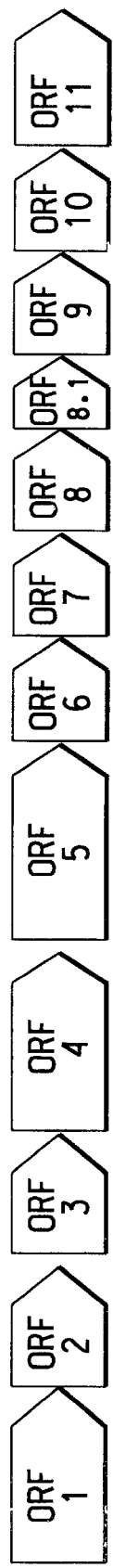
FIG. 6 is a diagram showing organization of the gene cluster involved in picric acid degradation.

The present invention relates to the isolation of genes encoding enzymes useful for the degradation of picric acid, and dinitrophenol. The relevant genes were isolated from a *Rhodococcus erythropolis* HL PM-1 (Lenke et al., *Appl. Environ. Microbiol.* 58:2933–2937 (1992)). Taxonomic identification of the *Rhodococcus erythropolis* HL PM-1 was accomplished on the basis of 16s rDNA analysis. Using RT-PCR many gene fragments covering several genes were identified (FIG. 5). The sequence information for these genes allowed for the identification of two clones from a large insert library that covered a single 12 kb gene cluster. All open reading frames (ORF's) residing on the gene cluster were sequenced. The organization of the ORF's as well as the putative identification of gene function is shown in FIG. 6.

The method for the identification of the genes in the 12 kb gene cluster as well as the relevant open reading frames is a modified RT-PCT protocol, and is based on the concept of mRNA differential display (McClelland et al., U.S. Pat. No. 5,487,985; Liang et al., *Nucleic Acids Res.* 22 (25):5763–4 (1994); Liang et al., *Nucleic Acids Res.* 21 (14):3269–75 (1993); Welsh et al., *Nucleic Acids Res.* 20 (19):4965–70 (1992)).

The instant method is a technique that compares the mRNAs sampled by arbitrary RT-PCR amplification between control and induced cells. For the analysis of bacterial genomes, typically only a small set of primers is used to generate many bands which are then analyzed by long, high resolution sequencing gels. Applicant has modified this approach using a larger set of about 240 primers analyzed on relatively short high resolution precast polyacrylamide gels. Each primer generates a RAPD pattern of an average of twenty DNA fragments. Theoretically, a set of 240 primers should generate about 4800 independent bands.

Figure 2:
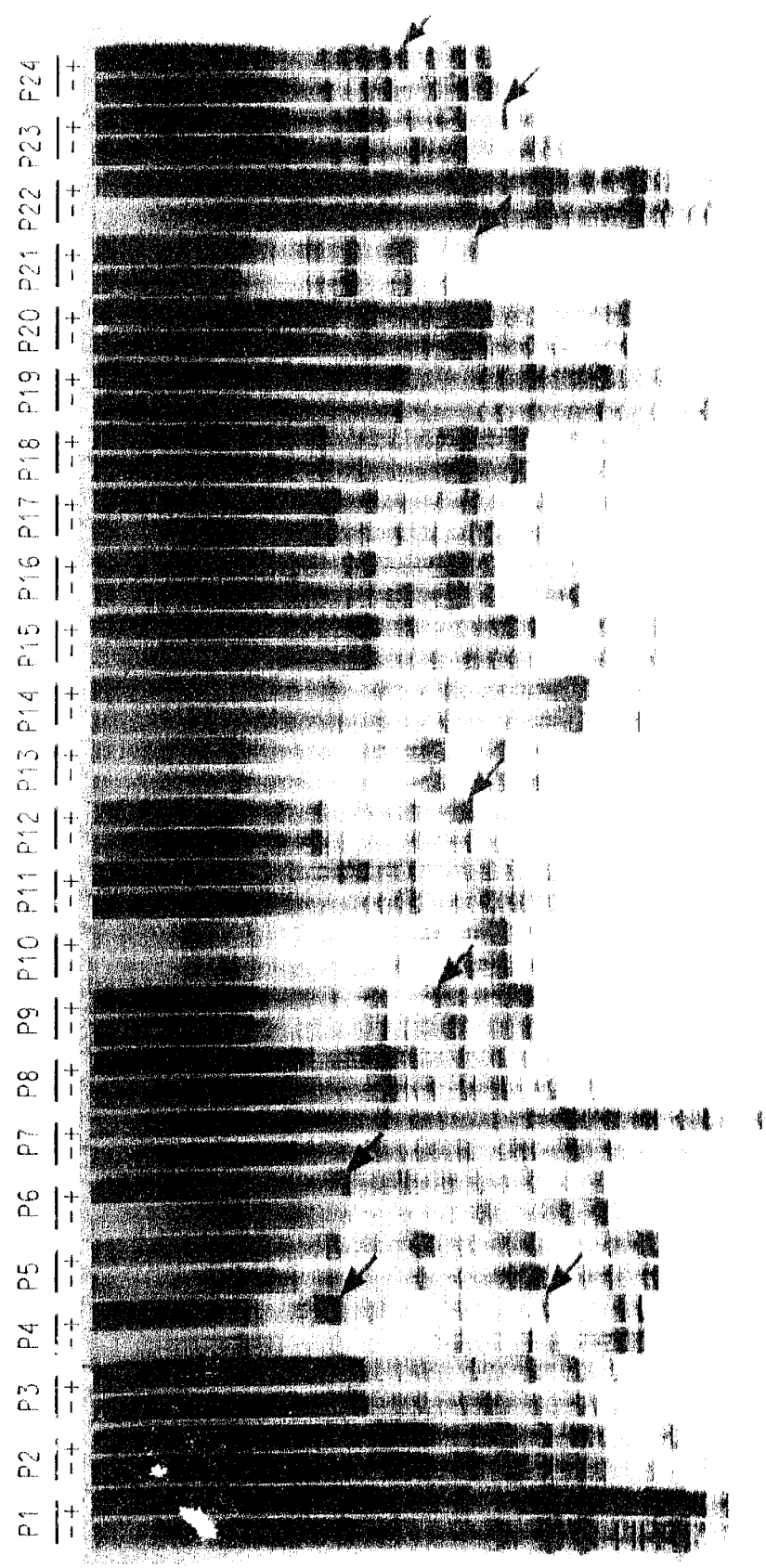
FIG. 2 shows gel separation of differentially expressed bands on a high resolution precast polyacrylamide gel.

While not intending to be limiting Applicants suggest that one explanation for the effectiveness of the large number of primers in the present method may be related to the probability of sampling of a metabolic operon in a typical prokaryote. For example, using high resolution precast acrylamide gels, each primer generates a RAPD pattern of at least of twenty clearly visible DNA fragments (FIG. 2). In theory, a set of 240 primers should generate around 4800 clearly visible independent bands (an underestimation). Assuming 1) a bacterial genome size of 4 million base pairs (Mbp) (i.e., *Escherichia coli* or *Bacillus subtilis*), 2) an average of one gene per kb, 3) an average of 3 genes per operon, and 4) that only 50% of the operons are expressed, the mRNA population may contain about 666 distinct multicistronic mRNA species at any given time. Assuming finally an equal probability of amplifying a rare message after 40 cycles of PCR (Mathieu-Daude et al., *Nucleic Acids Res.* 24:2080–2086 (1996)), the probability of not sampling a specific mRNA in a RT-PCR experiment generating 4800 RAPD bands is $(1-(1/666))^{4800}$ i.e., around 0.1%. Conversely the probability of sampling a specific operon is greater than 99.9% for genomes of 4 Mbp. The identification of ORF 8 and ORF 9 validate these assumptions.

The present method of differential display by high density sampling of prokaryotic mRNA may be viewed as having seven general steps: 1) growth and induction of cultures, 2) total RNA extraction, 3) primer and primer plate design, 4) arbitrarily primed reverse transcription and PCR amplification, 5) elution, reamplification and cloning of differentially expressed DNA fragments, 6) assembly of clones in contigs and sequence analysis and 7) identification of induced metabolic pathways.

Arbitrarily primed reverse transcription and PCR amplification are performed with the commercial enzyme kit from Gibco-BRL "Superscript One-Step RT-PCR System" that provide in a single tube the reverse transcriptase and the Taq polymerase in addition to a buffer system compatible with both reactions. The composition of the reverse transcriptase/Taq polymerase mix storage buffer and of the reaction mix are proprietary and not disclosed. The nature of the Reverse Transcriptase is not disclosed either. The reaction mix contains 0.4 mM of each dNTP and 2.4 mM $MgSO_4$ in addition to other components.

The primers used are a collection of 240 primers with the sequence 5'-CGGAGCAGATCGVVVVV-3' (SEQ ID NO:26) where VVVVV represents all the combinations of the three bases A, G and C at the last five positions of the 3' end. The 5' end sequence was designed as to have minimal homology towards both orientations of the 16S rDNA sequences from many organisms with widespread phylogenetic position in order to minimize non specific amplification of these abundant and stable RNA species.

The 240 primers are pre-aliquoted on five 96 well PCR plates. In each plate, each primer is placed in two adjacent positions as indicated below.

| A1 | A1 | A2 | A2 | A3 | A3 | A4 | A4 | A5 | A5 | A6 | A6 |
| --- | --- | --- | --- | --- | --- | --- | --- | --- | --- | --- | --- |
| A7 | A7 | A8 | A8 | A9 | A9 | A10 | A10 | A11 | A11 | A12 | A12 |
| A13 | A13 | A14 | A14 | A15 | A15 | A16 | A16 | A17 | A17 | A18 | A18 |
| A19 | A19 | A20 | A20 | A21 | A21 | A22 | A22 | A23 | A23 | A24 | A24 |
| A25 | A25 | A26 | A26 | A27 | A27 | A28 | A28 | A29 | A29 | A30 | A30 |
| A31 | A31 | A32 | A32 | A33 | A33 | A34 | A34 | A35 | A35 | A36 | A36 |

| | | | | | | | | | | | |
|---|---|---|---|---|---|---|---|---|---|---|---|
| A37 | A37 | A38 | A38 | A39 | A39 | A40 | A40 | A41 | A41 | A42 | A42 |
| A43 | A43 | A44 | A44 | A45 | A45 | A46 | A46 | A47 | A47 | A48 | A48 |

Typical RT-PCT is then performed using standard protocols well known in the art.

Separation and visualization of PCR products is carried out as follows: 5 µL out each 25 µL RT-PCR reaction are analyzed on precuts acrylamide gels (Excell gels Pharmacia Biotech). PCR products from control and Induced RNA generated from the same primers are analyzed side by side. The gels are stained with the Plus One DNA silver staining Kit (Pharmacia Biotech) to visualized the PCR Fragments then rinsed extensively with distilled water for one hour to remove the acetic acid used in the last step of the staining procedure. DNA fragments from control and induced lanes generated from the same primers are compared. Bands present in the induced lane but not in the control lane are excised with a scalpel.

Elution, reamplification and cloning of differentially expressed DNA fragments is carried out as follows. Each band excised from the gel is placed in a tube containing 50 µL of 10 mM KCl and 10 mM Tris-HCl pH 8.3 and heated to 95° C. for 1 h to allow some of DNA to diffuse out of the gel. Serial dilutions of the eluate (1/10) were used as template for a new PCR reaction using the following reactions: magnesium acetate (4 mM), dNTPs (0.2 mM), Taq polymerase buffer (Perkin Elmer), oligonucleotide primer (0.2 µM). The primer used for each reamplification was the one that had generated the DNA pattern.

Each reamplified fragment was cloned into the blue/white cloning vector pCR2.1-Topo (Invitrogen).

Four to eight clones from the cloning of each differentially expressed band were submitted to sequencing using the universal forward. Inserts that did not yield a complete sequence where sequenced on the other strand with the reverse universal primer.

The nucleotide sequences obtained where trimmed for vector, primer and low quality sequences, and aligned using the Sequencher program (Gene Code Corporation). The sequences of the assembled contigs are then compared to protein and nucleic acid sequence databases using the BLAST alignment program.

Once all contigs have been assembled, the number of bands having yielded clones included in the contig is plotted. Many contigs are composed of the sequence of distinct identical clones from the cloning of a single band. Such contigs may represent false positives, i.e., PCR bands not really differentially expressed but appearing so in our experiment, or PCR bands representing genes really differentially expressed but having been sampled by only one primer in the experiment. Some contigs are generated form the alignment of DNA sequences from bands amplified by distinct primers. Such events statistically less frequent are the indication that the genes identified are really differentially expressed. Furthermore, distinct contigs showing homology to different part of the same protein sequence can be clustered and also indicate that the genes identified are really differentially expressed.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures required for PCR amplification, DNA modifications by endo- and exonucleases for generating desired ends for cloning of DNA, ligations, and bacterial transformation are well known in the art. Standard molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring, N.Y., 1984 and by Ausubel et al., *Current Protocols in Molecular Biology*; Greene Publishing and Wiley-Interscience; 1987.

Materials and methods suitable for the maintenance and growth of bacterial cultures are well known in the art. Techniques suitable for use in the following examples may be found as set out in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C., 1994 or by Brock, T. D.; *Biotechnology: A Textbook of Industrial Microbiology*, 2nd ed.; Sinauer Associates: Sunderland, Mass., 1989. All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified. Other materials were obtained from Qiagen, Valencia, Calif.; Roche Molecular Biochemicals, Indianapolis, Ind.; and Invitrogen, Carlsbad, Calif.

PCR reactions were run on GeneAMP PCR System 9700 using Amplitaq or Amplitaq Gold enzymes (PE Applied Biosystems, Foster City, Calif.). The cycling conditions and reactions were standardized according to manufacture's instructions.

Precast polyacrylamide Excell gels and the "Plus-One" silver stain kit were from Amersham Pharmacia Biotech Piscataway, N.J.

Analysis of genetic sequences were performed with the sequence assembly program Sequencher (GeneCodes corp., Ann Arbor Mich.). Sequence similarities were analyzed with the BLAST program at NCBI. In any case where sequnece analysis software program parameters were not prompted for, in these or any other program, default values were used, unless otherwise specified.

The meaning of abbreviations is as follows: "sec" means second(s), "min" means minute(s), "h" means hour(s), "d" means day(s), "µL" means microliter, "mL" means milliliters, "L" means liters, "mM" means millimolar, "M" means molar, "mmol" means millimole(s), "g" means gram, "µg" means microgram and "ng" means nanogram.

Bacterial Strains

The bacterial strain used for these experiments is a derivative of *Rhodococcus erythropolis* HL 24-2 capable of degrading picric acid as well as dinitrophenol (Lenke et al., *Appl. Environ. Microbiol.* 58:2933–2937 (1992)).

R2A Medium

Per liter: glucose 0.5 g, starch 0.5 g, sodium pyruvate 0.3 g, yeast extract 0.5 g, peptone 0.5 g, casein hydrolyzate 0.5 g, magnesium sulfate 0.024 g, potassium phosphate 0.3 g pH 7.2.

Minimal DNP Medium

Per liter: 20 mM acetate, 54 mM $NaPO_4$ buffer pH 7.2 20 mg/L Fe(III)-citrate, 1 g/L $MgSO_4$ $7H_2O$, 50 mg/L $CaCl_2$ $2H_2O$ and 1 mL trace element solution (Bruhn et al., *Appl. Environ. Microbiol.* 53:208–210 (1987)).

Total RNA Extraction

Cell disruption was performed mechanically in bead beater by zirconia/silica beads (Biospec Products, Bartlesville, Okla.) in the presence of a denaturant (i.e., acid phenol or Guanidinium Thiocyanate in the RNeasy kit). The total RNA was extracted using the RNeasy kit from Qiagen or with buffered water-saturated phenol at pH 5 and extracted successively with acid phenol, and a mixture of phenol/chloroform/isoamyl alcohol. Each RNA preparation is resuspended in 500 μL of DEPC treated $H_2O$, and treated with RNase-free DNase (Roche). Typically a 10 mL culture harvested at $A_{600nm}=1$ yields about 10–20 mg of cells wet weight that contain 400–800 ng of total RNA (assuming dry weight is 20% wet weight, RNA (stable+messenger RNA) is 20% of dry weight). The RNA extracted from a 10 mL culture is sufficient to perform the 240 RT-PCR reactions of a complete experiment.

Primer Design

Primers were applied to 96 well plates as follows. The 240 primers are pre-aliquoted on five 96 well PCR plates. In each plate, 4 μL of each primer (2.5 μM) was placed in two adjacent positions as indicated below.

| Plate #1 containing primers number A1 to A48 | | | | | | | | | | | |
|---|---|---|---|---|---|---|---|---|---|---|---|
| A1 | A1 | A2 | A2 | A3 | A3 | A4 | A4 | A5 | A5 | A6 | A6 |
| A7 | A7 | A8 | A8 | A9 | A9 | A10 | A10 | A11 | A11 | A12 | A12 |
| A13 | A13 | A14 | A14 | A15 | A15 | A16 | A16 | A17 | A17 | A18 | A18 |
| A19 | A19 | A20 | A20 | A21 | A21 | A22 | A22 | A23 | A23 | A24 | A24 |
| A25 | A25 | A26 | A26 | A27 | A27 | A28 | A28 | A29 | A29 | A30 | A30 |
| A31 | A31 | A32 | A32 | A33 | A33 | A34 | A34 | A35 | A35 | A36 | A36 |
| A37 | A37 | A38 | A38 | A39 | A39 | A40 | A40 | A41 | A41 | A42 | A42 |
| A43 | A43 | A44 | A44 | A45 | A45 | A46 | A46 | A47 | A47 | A48 | A48 |

The ordering of the primers on the plates corresponded to the order of the systematic sequence variations in the design of the 3' end of the sequence CGGAGCAGATCGVVVVV (SEQ ID NO:26) (where VVVVV represents all the combinations of the three bases A, G and C at the last five positions of the 3' end). The following pattern was followed for each of the plates where the position of the variable base refers to primer as given in SEQ ID NO:26:

| | Position 13 | Position 14 | Position 15 | Position 16 | Position 17 |
|---|---|---|---|---|---|
| A1 | A | A | A | A | A |
| A2 | A | A | A | A | C |
| A3 | A | A | A | A | G |
| A4 | A | A | A | C | A |
| A5 | A | A | A | C | C |
| A6 | A | A | A | C | G |
| A7 | A | A | A | G | A |
| A8 | A | A | A | G | C |
| A9 | A | A | A | G | G |
| A10 | A | A | C | A | A |
| A11 etc . . . | | | | | |

The algorithm of Breslauer et al. (*Proc. Natl. Acad. Sci. USA* 83:3746–3750 (1986)) was used to calculate the Tm of the primers in the collection. In this fashion the 240 primers were ranked by increasing Tm and separated into five 96-well plates, each corresponding to a narrower Tm interval.

RT-PCR Reactions

The 480 RT-PCR reactions were performed in 96 well sealed reaction plates (PE Applied Biosystems, Foster City, Calif.) in a GeneAmp PCR System 9700 (PE Applied Biosystems, Foster City, Calif.). The enzyme used were the Ampli Taq DNA polymerase (PE Applied Biosystems, Foster City, Calif.) and the Plus One RT-PCR kit (Gibco BRL).

Separation and Visualization of PCR Products

5 μL out each 25 μL RT-PCR reaction is analyzed on precast acrylamide gels (Excell gels Pharmacia Biotech). PCR products from control and induced RNA generated from the same primers are analyzed and compared.

EXAMPLE 1

Induction of DNP Degradation Pathway by DNP

Figure 1:
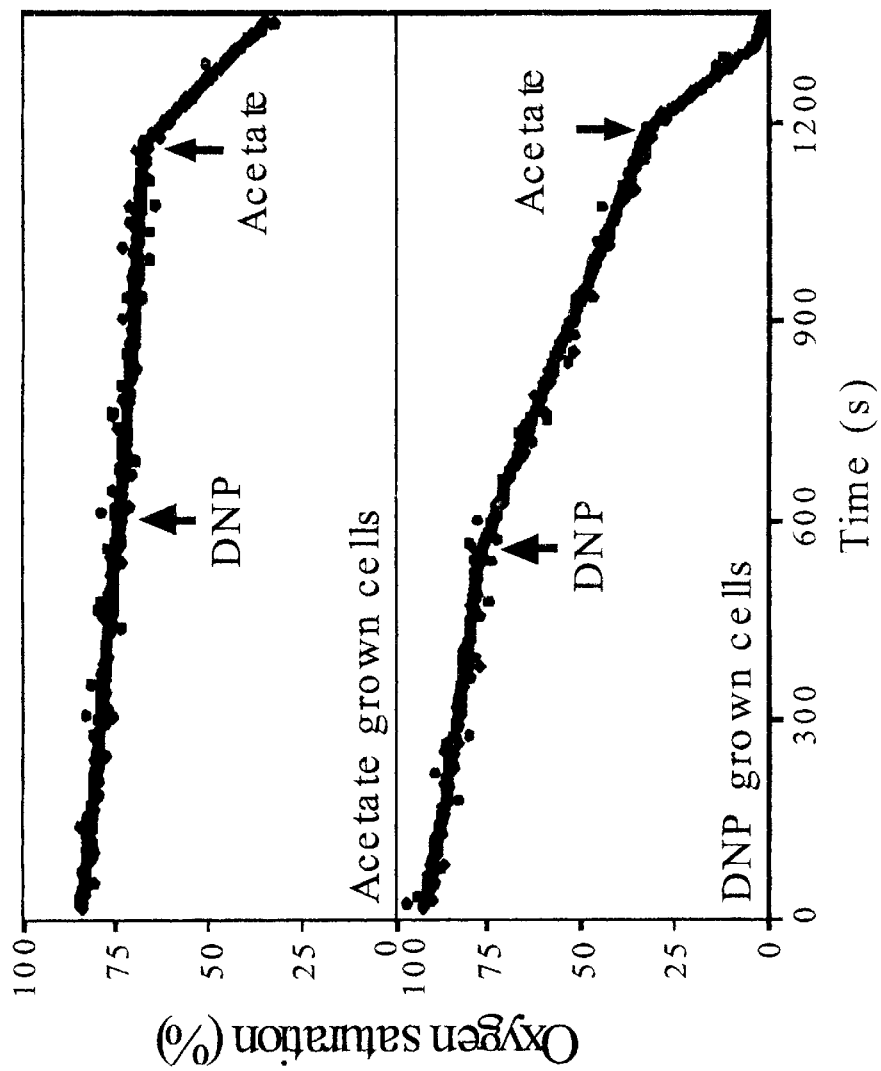
FIG. 1 is a diagram showing the induction of the degradation of picric acid and DNP by DNP in respirometry experiments.

A culture of *Rhodococcus erythropolis* strain HL PM-1 grown overnight at 30° C. in minimal medium (20 mM acetate, 54 mM $NaPO_4$ buffer pH 7.2, 20 mg/L Fe(III)-citrate, 1 g/L $MgSO_4$ $7H_2O$, 50 mg/L $CaCl_2$ $2H_2O$ and 1 mL trace element solution (Bruhn et al., *Appl. Environ. Microbiol.* 53:208–210 (1987)) to an absoption of 1.9 at 546 nm was diluted 20 fold in two 100 mL cultures, one of which received 0.55 mM dinitrophenol (DNP), the inducer of DNP and picric acid degradation. To characterize the induction of the DNP degradation pathway, cultures were then chilled on iced, harvested by centrifugation and washed three times with ice cold mineral medium. Cells were finally resuspended to an absorption of 1.5 at 546 nm and kept on ice until assayed. 0.5 mL of each culture was placed in a water jacketed respirometry cell equipped with an oxygen electrode (Yellow Springs Instruments Co., Yellow Springs, Ohio) and with 5 mL of air saturated mineral medium at 30° C. After establishing the baseline respiration for each cell suspension, acetate or DNP was added to the final concentration of 0.55 mM and the rate of $O_2$ consumption was further monitored (FIG. 1). Control cells grown in the absence of DNP did not show an increase of respiration upon addition of DNP but did upon addition of acetate. In contrast cells exposed to DNP for 6 h increased their respiration upon addition of DNP indication. These results indicate that the picric acid degradation pathway is induced and the enzymes responsible for this degradation are expressed.

EXAMPLE 2

Isolation of RNA from Control and Induced for PCR Reactions

Two 10 mL cultures of Rhodococcus erythropolis strain HM-PM1 were grown and induced as described in Example 1. Each culture was chilled rapidly in an ice/water bath and transferred to a 15 mL tube. Cells were collected by centrifugation for 2 min at 12,000×g in a rotor chilled to −4° C. The supernatants were discarded, the pellets resuspended in 0.7 mL of ice cold solution of 1% SDS and 100 mM sodium acetate at pH 5 and transferred to a 2 mL tube containing 0.7 mL of aqueous phenol (pH 5) and 0.3 mL of 0.5 mm zirconia beads (Biospec Products, Bartlesville, Okla.). The tubes were placed in a bead beater (Biospec Products, Bartlesville, Okla.) and disrupted at 2400 beats per min for two min.

Following the disruption of the cells, the liquid phases of the tubes were transferred to new microfuge tubes and the phases separated by centrifugation for 3 min at 15,000×g. The aqueous phase containing total RNA was extracted twice with phenol at pH 5 and twice with a mixture of phenol/chloroform/isoamyl alcohol (pH 7.5) until a precipitate was no longer visible at the phenol/water interface. Nucleic acids were recovered from the aqueous phase by ethanol precipitation with three volumes of ethanol, and the pellet resuspended in 0.5 mL of diethyl pyrocarbonate (DEPC) treated water. DNA was digested by 6 units of RNAse-free DNAse (Roche Molecular Biochemicals, Indianapolis, Ind.) for 1 h at 37° C. The total RNA solution was extracted twice with phenol/chloroform/isoamyl alcohol (pH 7.5), recovered by ethanol precipitation and resuspended in 1 mL of DEPC treated water to an approximate concentration of 0.2 mg per mL. The absence of DNA in the RNA preparation was verified in that ramdomly amplified PCR DNA fragments could not be generated by the Taq polymerase unless the reverse transcriptase was also present.

In other experiments, the cell pellets were resuspended in 0.3 mL of the chaotropic guanidium isothiocyanate buffer provided by the RNA extraction kit (Qiagen, Valencia, Calif.) and transferred in a separate 2 mL tube containing 0.3 mL of 0.5 mm zirconia beads (Biospec Products, Bartlesville, Okla.). The tubes were placed in a bead beater (Biospec Products, Bartlesville, Okla.) and disrupted at 2400 beats per min for two min. The total RNA was then extracted with the RNeasy kit from Qiagen. Each RNA preparation was then resuspended in 500 μL of DEPC treated $H_2O$ and treated with RNAse-free DNase (2U of DNase/100 μL RNA) for 1 h at 37° C. to remove DNA contamination.

EXAMPLE 3

Performance of RT-PCR using 240 Oligonucleotide Fragments

The complete RT-PCR experiment of 480 reactions (240 primers tested on two RNA preparations) were performed in five 96-well format, each containing 5 μL of 2.5 μM of 48 arbitrary primers prealiquoted as described above. A RT-PCR reaction master mix based on the RT-PCR kit "Superscript One-Step RT-PCR System" (Gibco/BRL Gaithersburg, Md.) was prepared on ice as follows:

|  | Per 25 μL reaction | Per 96 + 8 reactions |
| --- | --- | --- |
| 2X reaction mix | 12.5 μL | 1300 μL |
| $H_2O$ | 6.0 μL | 624 μL |
| RT/Taq | 0.5 μL | 52 μL |
| Total | 19.0 μL | 1976 μL |

The master mix was split in two tubes receiving 988 μL each. Fifty-two μL of total RNA (20–100 ng/μL) from the control culture was added to one of the tubes and 52 μL of total RNA (20–100 ng/μL) from the induced culture were added to the other tube. Using a multipipetter, 20 μL of the reaction mix containing the control RNA template were added to the tubes in the odd number columns of the 96 well PCR plate and 24 μL of the reaction mix containing the "induced" RNA template were added to the tubes in the even number columns of the 96 well PCR plate, each plate containing 5 μl of prealiquoted primers. All manipulations were performed on ice. Heat denaturation of the RNA to remove RNA secondary structure prior to the addition of the reverse transcriptase was omitted in order to bias against the annealing of the arbitrary primers to the stably folded ribosomal RNAs.

The PCR machine was programmed as follows: 4° C. for 2 min; ramp from 4° C. to 37° C. for 5 min; hold at 37° C. for 1 h; 95° C. for 3 min, 1 cycle; 94° C. for 1 min, 40° C. for 5 min, 72° C. for 5 min, 1 cycle; 94° C. for 1 min, 60° C. for 1 min, 72° C. for 1 min, 40 cycles; 72° C. for 5 min, 1 cycle; hold at 4° C. To initiate the reaction, the PCR plate was transferred from the ice to the PCR machine when the block was at 4° C.

EXAMPLE 4

Electrophoresis Analysis and Visualization of PCR Products and Identification of Differentially Expressed Bands 240 pairs of RT-PCR reactions were primed by the collection of 240 oligonucleotides (as described above). Pairs of RT-PCR reaction (corresponding to an RT-PCR sampling of the mRNA from control and induced cells) were analyzed on 10 precast acrylamide gels, 48 lanes per gels (Excell gels, Amersham Pharmacia Biotech, Piscataway, N.J.). PCR products from control and induced RNA generated from the same primers were analyzed side by side. The PCR fragments were visualized by staining gels with the "Plus One" DNA silver staining Kit (Amersham Pharmacia Biotech, Piscataway, N.J.), shown in FIG. 2. In this manner, a series of 240 RT-PCR reactions were performed for each RNA sample. On average each RT-PCR reaction yielded ~20 clearly visible DNA bands (FIG. 2) leading to a total number of bands about 5000. RAPD Patterns generated from the RNA of control and DNP-induced cells using the same primer are extremely similar. Examples of differentially amplified bands are identified with an arrow in FIG. 2.

EXAMPLE 5

Elution and Reamplification of the DNA RT-PCR Band

Of the bands visualized in Example 4, 48 differentially amplified DNA fragment bands were excised from the silver stained gel with a razor blade and placed in a tube containing 25 μL of elution buffer: 20 mM NaCN, 20 mM Tris-HCl pH 8, 50 mM KCl, 0.05% NP40 and heated to 95° C. for 20 min to allow some of DNA to diffuse out of the gel. The eluate solution was used in a PCR reaction and consisted of: 5 μL 10×PCR buffer, 5 μL band elution supernatant, 5 μL 2.5 μM primer, 5 μL dNTPs at 0.25 mM, 30 μL water and 5 μL Taq polymerase.

When the reamplification used the arbitrary primer that had generated the RAPD pattern ("specific primer"), the PCR machine was programmed as follows: 94° C. for 5 min; 94° C. for 1 min; 55° C. for 1 min; 72° C. for 1 min for 20 cycles, 72° C. for 7 min hold; 4° C. hold. When the cyanide was not incorporated in the elution buffer, the reamplification of the band often needed more PCR cycles.

In other experiments when the reamplification used the universal reamplification primer (5'-AGTCCACGGAGCATATCG-3' (SEQ ID NO:27) was used, the PCR machine was programmed as follows: 94° C. for 5 min; 94° C. for 30 sec; 40° C. for 1 min; ramp to 72° C. in 5 min; 72° C. for 5 min for 5 cycles; 94° C. for 1 min, 55° C. for 1 min; 72° C. for 1 min for 40 cycles; 72° C. for 5 min, hold at 4° C.

Figure 3:
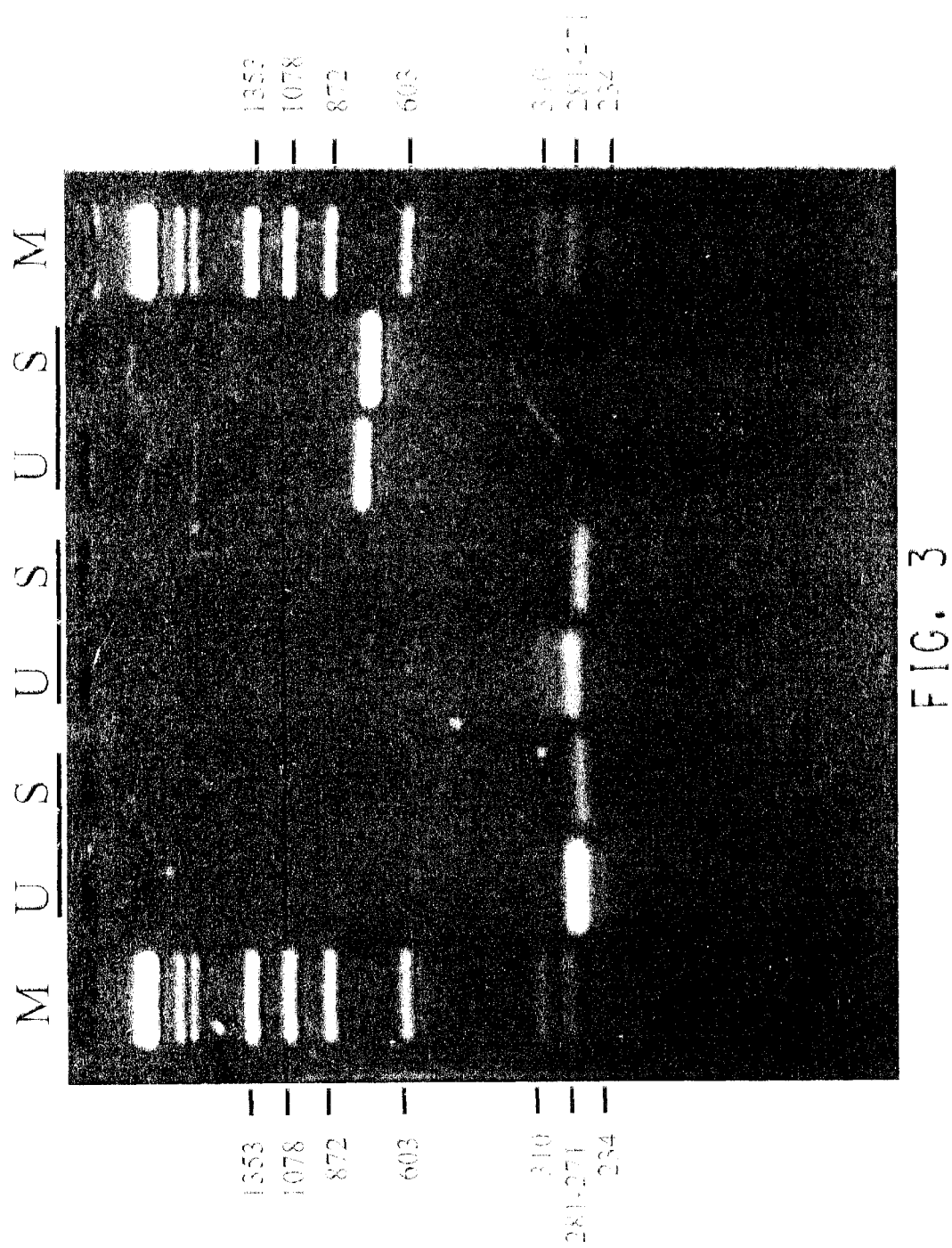
FIG. 3 show a gel separation of DNA bands reamplified from DNA eluted from excised RT-PCR bands from silver stained polyacrylamide gels.

Analysis of the reamplified fragments was performed on 1% agarose gel stained with ethidium bromide as shown for three different fragments in FIG. 3. The reamplification of a differentially amplified band eluted from the polyacrylamide gel yielded the same PCR fragment with both reamplification primer. DNA fragments reamplified with the universal primer (noted U) are slightly longer than those reamplified with the specific primer (noted S) because they include 8 additional bases at each end present in the universal reamplification primer.

EXAMPLE 6

Figure 4:
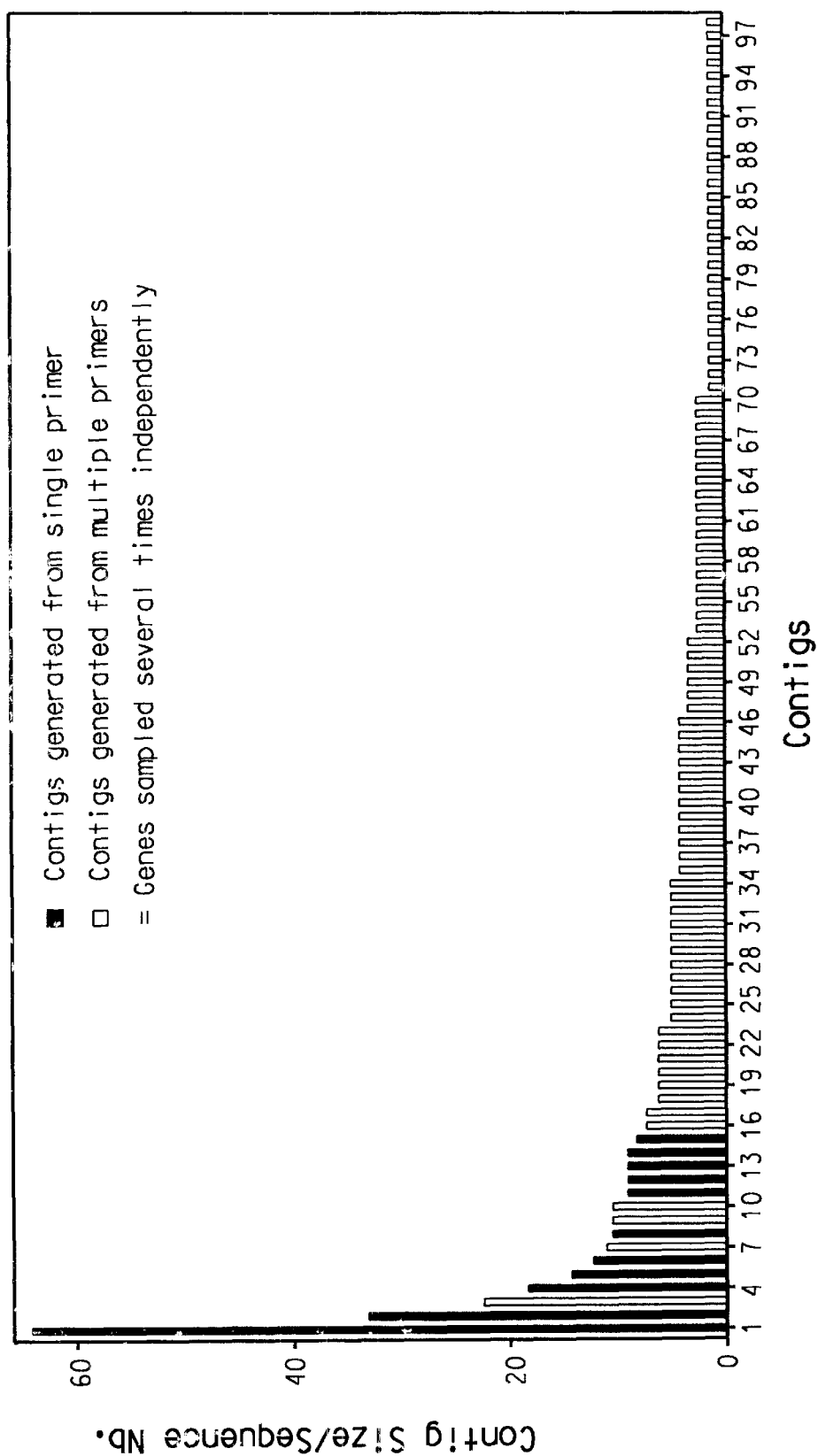
FIG. 4 is a diagram showing the distribution of number of DNA sequences assembled in each contig.

Cloning, Sequencing and Contig Assembly of the Differentially Expressed DNA Fragments 48 RAPD fragments differentially amplified in the RT-PCR reactions from "induced" samples but not in the control RT-PCR reactions were identified and reamplified as described in Experiment 5. The product of each reamplification was cloned in the vector pCR2.1 (Invitrogen) and eight clones were isolated from the cloning of each reamplified band. The nucleotide sequence of each insert was determined, trimmed for vector, primer and low quality sequences and aligned with the alignment program, "Sequencher" (Gene Code Corp., Ann Arbor, Mich.) and assembled into contigs. The assembly parameters were 80% identity over 50 bases. The number of sequences comprised in each contig were plotted (FIG. 4) and the nucleotide sequence of the contigs assembled from DNA fragments generated in independent RT-PCR reactions was then compared to nucleic acid and amino acid sequences in the GenBank database.

Several contigs were assembled from the sequence of DNA bands generated in several independent RT-PCR reactions. These contigs, named according to that of homologous sequences, are listed in Table 1.

TABLE 1

Homologies of contigs assembled from more than one band and more than one primer

| Best Homology | Multiplicity of Sampling Size | Contig |
|---|---|---|
| F420-dependent Dehydrogenase | 6 Primers/9 Bands | 1.7 kb |
| Aldehyde Dehydrogenase | 4 Primers/4 Bands | 0.7 kb |
| F420-dependent Oxidoreductase | 4 Primers/4 Bands | 1.1 kb |
| RNA Polymerase a Subunit | 4 Primers/4 Bands | 1.1 kb |
| 16S rRNA | 4 Primers/4 Bands | 1.1 kb |
| 23S rRNA | 4 Primers/4 Bands | 1.2 kb |
| ATP Synthase | 3 Primers/3 Bands | 0.9 kb |
| Transcriptional Regulator | 2 Primers/4 Bands | 0.8 kb |
| Transcription Factor | 2 Primers/2 Bands | 0.7 kb |

Among these contigs, two showed homology to F420-dependent enzymes suggesting the involvement of Factor F420 in the degradation of the picric acid. The complete sequence of a F420-dependent dehydrogenase (FIG. 6, ORF 3) was generated directly by the overlap of the sequence of differentially amplified bands which allowed the synthesis of PCR primers for the direct cloning of this gene. The partial sequence of a second F420-dependent gene encoding an F420/NADPH oxidoreductase was also identified.

Oligonucleotide primers corresponding to the ends of the F420-dependent Dehydrogenase gene (FIG. 6, ORF 3) were next used to identify two clones from a large (>10 kb) insert plasmid library that carried that gene. The subsequent sequencing of these clones showed that four of the contigs identified (Table 1) were linked to a single gene cluster (FIG. 6). This 12 kb sequence was sampled 21 times out of the 48 differentially expressed bands identified. Within that sequence, a third gene (FIG. 6, ORF 9), the 3' end sequence (180 bp) of which had been sampled by differential display, encoding for an F420-dependent dehydrogenase was identified on the basis of sequence similarities. The 12 kb gene cluster encodes for 10 genes. The beginning and the end of the genes were determined by comparison with homologous sequences. Where possible, an initiation codon (ATG, GTG, or TTG) was chosen which was preceded by an upstream ribosome binding site sequence (optimally 5–13 bp before the initiation codon). If this could not be identified the most upstream initiation codon was used. The best homologies to each ORF, and thus their putative function in the degradation pathway of picric acid are listed in Table 2. Finally, a contig assembled from the sequences corresponding to the cloning of a single differentially amplified DNA fragment matched the sequence of ORF 11 (acyl-CoA dehydrogenase).

TABLE 2

| ORF | Similarity Identified | SEQ ID Nucl. | SEQ ID Peptide | % Identity[a] | % Similarity[b] | E-value[c] | Citation |
|---|---|---|---|---|---|---|---|
| 1 | sp\|Q10550\|YZ18__MYCTU Putative regulatory protein CY31.18C [*Mycobacterium tuberculosis*] | 2 | 3 | 32% + 45% | 45% + 58% | 3c-25 + 1e-13 | Murphy, et al. direct submission May 1996 |
| 2 | (AE001036) L-carnitine dehydratase [*Archacoglobus fulgidus*] | 4 | 5 | 34% | 52% | 9e-51 | Klenk, H. P. et al. Nature 390 (6658), 364–370 (1997) |
| 3 | >pir\|\|E64491 N5,N10-methylene tetrahydromethanopterin reductase | 6 | 7 | 24% | 42% | 6e-12 | Bult, C. J. et al Science 273 (5278), |

TABLE 2-continued

| ORF | Similarity Identified | SEQ ID Nucl. | SEQ ID Peptide | % Identity[a] | % Similarity[b] | E-value[c] | Citation |
|---|---|---|---|---|---|---|---|
| 4 | [Methanococcus jannaschii] (U24215) p-cumic aldehyde dehydrogenase [Pseudomonas putida] | 8 | 9 | 44% | 60% | 2e-99 | 1058–1073 (1996) Eaton, R. W. J. Bacteriol. 178 (5), 1351–1362 (1996) |
| 5 | >sp|P39062| Acetate CoA ligase [Bacillus subtilis] | 10 | 11 | 27% | 42% | 5e-42 | Grundy, F. J et al. Mol. Microbiol. 10:259–271(1993). |
| 6 | (AJ243528) putative glyoxalase I [Triticum] | 12 | 13 | 26% | 38% | 0.001 | Direct Submission - g7619802 |
| 7 | (AE000277) Transcriptional Regulator Kdgr [Escherichia coli] | 14 | 15 | 26% | 42% | 3e-11 | Blattner, F. R., et al. Rb SCIENCE 277: 1453–1474(1997). |
| 8 | >sp|O26350| F420-Dependent NADP Reductase (AE000811) [Methanobacterium thermoautotrophicum] | 16 | 17 | 32% | 44% | 1e-18 | Smith, D. R. et al., J. Bacteriol. 179:7135–7155 (1997). |
| 8.1 | (AL355913) putative translation initiation factor- Streptomyces coelicolor | 18 | 19 | 38% | 48% | 1e-04 | Redenbach, M., et al., Mol. Microbiol. 21(1), 77–96 (1996) |
| 9 | >gi|2649522 (AE001029) N5,N10-Methylenetetrahydromethanopterin Reductase [Archaeoglobus fulgidus] | 20 | 21 | 28% | 46% | 7e-26 | Klenk, H. P et al. Nature 390 (6658), 364–370 (1997) |
| 10 | >gi|97441|pir|S19026 Enoyl-CoA Hydratase [Rhodobacter capsulatus] | 22 | 23 | 26% | 38% | 9e-08 | Beckman, D. L et al.; Gene 107:171–172(1991). |
| 11 | gi|2649289 (AE001015) acyl-CoA dehydrogenase (acd-9) [Archacoglobus fulgidus] | 24 | 25 | 32% | 54% | 5e-44 | Klenk, H. P. et al. Nature 390 (6658), 364–370 (1997) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

EXAMPLE 7

Figure 7:
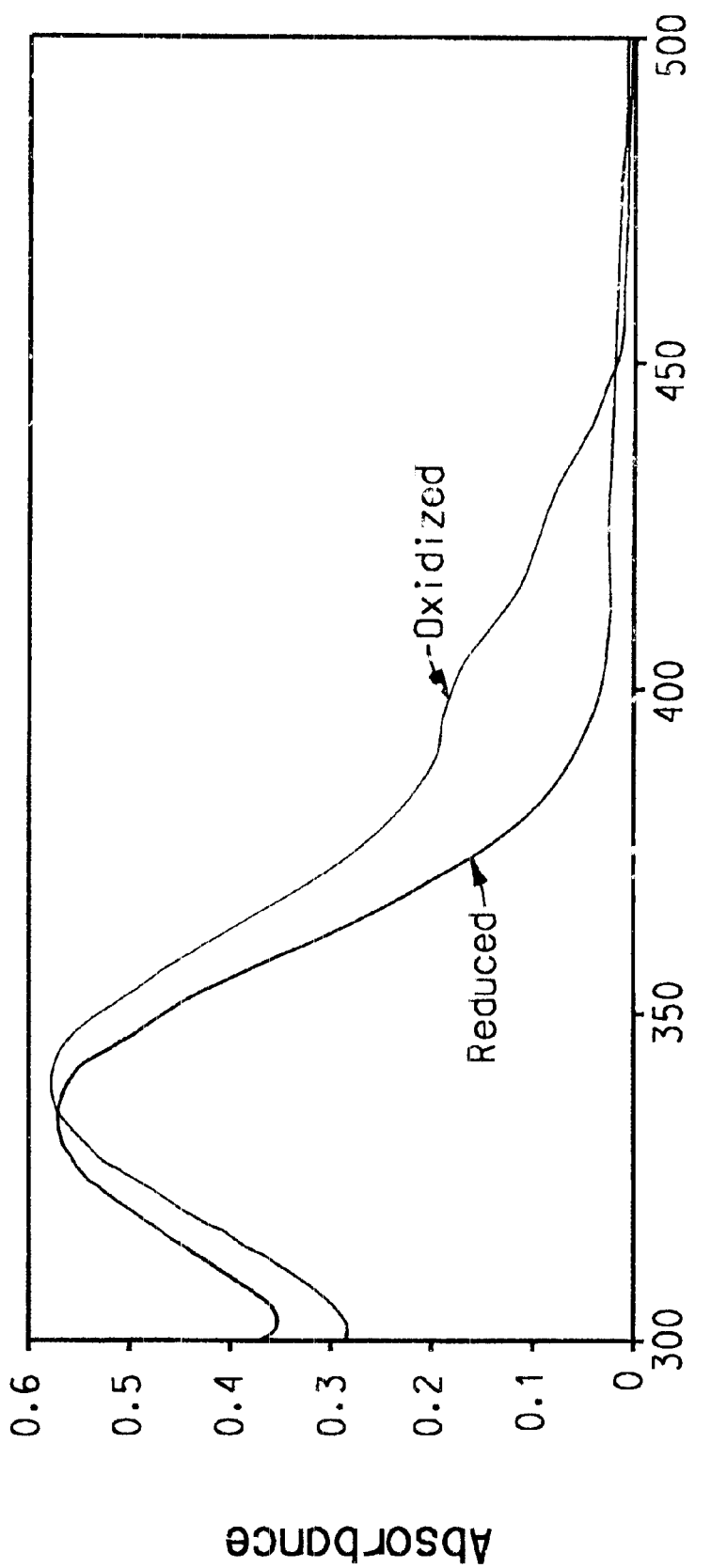
FIG. 7 is a diagram showing the activity of the cloned F420/NADPH oxidoreductase (ORF8).

Cloning and Expression of Two F420-dependent Genes Involved in the Degradation of Picric Acid To confirm that the gene cluster identified by differential display was indeed involved in the degradation of nitrophenols, the gene for two F420-dependent enzymes were cloned and expressed in E. coli. ORF 8 was shown to encode an F420/NADPH oxido-reductase. FIG. 7 shows the spectral changes of a solution of NADPH (0.075 mM) and F420 (0.0025 mM) in 50 mM sodium citrate buffer (pH 5.5) upon addition of cell extracts of E. coli expressing the F420/NADPH oxidoreductase (ORF 8). The characteristic disappearance of absorbance peaks at 400 and 420 nM corresponds to the reduction of factor F420. The activity of the enzyme encoded by ORF 9 was shown spectrophotometrically in a cuvette containing NADPH (0.075 mM), F420 (0.0025 mM) DNP or picric acid (0.025 mM) and E. coli extracts expressing the F420/NADPH oxidoreductase (ORF 8). The F420/NADPH oxidoreductase was added as a reagent to reduce F420 with NADPH. Upon addition of E. coli extracts expressing the F420-dependent dehydrogenase (ORF 9), reduced F420 reduces picric acid (FIG. 8A) or dinitrophenol (FIG. 8B). The spectral changes match those reported for the formation of the respective Meisenheimer complexes of picric acid and dinitrophenol (Behrend et al., Appl. Environ. Microbiol. 65:1372–1377 (1999)), thus confirming that ORF 9 encodes for the F420-dependent picric/dinitrophenol reductase.

What is claimed is:

1. An isolated nucleic acid fragment encoding an F420-dependent picric/2,4-dinitrophenol dehydrogenase selected from the group consisting of:
   (a) an isolated nucleic acid fragment encoding the amino acid sequence as set forth in SEQ ID NO:21, or an enzymatically acitive fragment thereof; and
   (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid fragment that is completely complementary to (a) or (b).

2. The isolated nucleic acid fragment of claim 1 as set forth in SEQ ID NO:20.

3. An isolated nucleic acid molecule comprising a first nucleotide sequence encoding a polypeptide having F420-dependant picric/2,4-dinitrophenol dehydrogenase activity of at least 350 amino acids that has at least 70% identify based on the Clustal method of alignment when compared to a polypeptide having the sequence as set forth in SEQ ID NO:21, or a second nucleotide sequence comprising the complement of the first nucleotide sequence.

4. A chimeric gene comprising the isolated nucleic acid fragment of claim 1 operably linked to suitable regulatory sequences.

5. A transformed cell comprising the chimeric gene of claim 4.

6. The transformed cell of claim 5 wherein the cell is selected from the group consisting of bacteria, yeast, and filamentous fungi.

7. The transformed cell of claim 6 wherein the cell is selected from the group consisting of Mycobacterium, Rhodococcus, Streptomyces, Nocardia, Arthrobacter, Methanobacterium, Methanococcus, Methanosarcina, Archaeoglobus, Aspergillus, Saccharomyces, Pichia, Candida, Hansenula, Salmonella, Bacillus, Acinetobacter, Escherichia and Pseudomonas.

* * * * *